(12) United States Patent
Kimura et al.

(10) Patent No.: US 12,274,816 B2
(45) Date of Patent: Apr. 15, 2025

(54) AIR PURIFICATION SYSTEM AND PROTECTIVE CLOTHING

(71) Applicant: Integral Geometry Science Inc., Hyogo (JP)

(72) Inventors: Kenjiro Kimura, Hyogo (JP); Noriaki Kimura, Hyogo (JP)

(73) Assignee: INTEGRAL GEOMETRY SCIENCE INC., Hyogo (JP)

( * ) Notice: Subject to any disclaimer, the term of this patent is extended or adjusted under 35 U.S.C. 154(b) by 379 days.

(21) Appl. No.: 17/924,548

(22) PCT Filed: May 24, 2021

(86) PCT No.: PCT/JP2021/019586
§ 371 (c)(1),
(2) Date: Nov. 10, 2022

(87) PCT Pub. No.: WO2021/241488
PCT Pub. Date: Dec. 2, 2021

(65) Prior Publication Data
US 2023/0285625 A1    Sep. 14, 2023

(30) Foreign Application Priority Data
May 26, 2020    (JP) .................................. 2020-091606

(51) Int. Cl.
*A61L 9/16*     (2006.01)
*A61L 9/22*     (2006.01)
*H05H 1/24*     (2006.01)

(52) U.S. Cl.
CPC ............ *A61L 9/16* (2013.01); *A61L 2209/111* (2013.01); *A61L 2209/14* (2013.01); *A61L 2209/212* (2013.01)

(58) Field of Classification Search
CPC ................ A61L 9/16; A61L 9/22; H05H 1/24
See application file for complete search history.

(56) References Cited

U.S. PATENT DOCUMENTS

2010/0040516 A1*    2/2010   Kimura ................. F01N 3/0892
                                                                422/186.29

FOREIGN PATENT DOCUMENTS

| EP | 1293216 | 3/2003 |
|---|---|---|
| JP | 2002-95731 | 4/2002 |

(Continued)

OTHER PUBLICATIONS

International Search Report (ISR) issued on Jul. 6, 2021 in International (PCT) Application No. PCT/JP2021/019586.

(Continued)

*Primary Examiner* — Kevin Joyner
(74) *Attorney, Agent, or Firm* — Wenderoth, Lind & Ponack, L.L.P.

(57) ABSTRACT

An air purification system includes a linear electrode that generates electromagnetic resonance; an electric field probe that measures the electric field intensity; and a controller that controls power supplied to the linear electrode. The controller adjusts the frequency of the power supplied to the linear electrode and the position at which the power is supplied to the linear electrode, to maximize an output value of a signal indicating the electric field intensity. Feedback control is performed to make the amount of ozone always constant, by monitoring the amount of ozone generated and adjusting the amplitude modulation of the power supplied, so that ozone necessary for decomposing viruses is generated but harmful nitrogen oxides are not generated as a result of applying, to gas molecules contained in influent gas, an energy that is at least the dissociation energy of oxygen molecules and no greater than the dissociation energy of nitrogen molecules.

13 Claims, 16 Drawing Sheets

(56) References Cited

FOREIGN PATENT DOCUMENTS

| | | |
|---|---|---|
| JP | 2006-255064 | 9/2006 |
| JP | 2008-34174 | 2/2008 |
| JP | 2010-25049 | 2/2010 |
| JP | 2011-122526 | 6/2011 |
| JP | 2012-21760 | 2/2012 |
| JP | 2012-167614 | 9/2012 |
| JP | 2018-117843 | 8/2018 |
| JP | 2020-49209 | 4/2020 |

OTHER PUBLICATIONS

Toshiaki Yamamoto, et al., "Complete NOx Removal Technology Using Nonequilibrium Plasma and Chemical Process (Performances of Ordinary and Barrier Type Plasma Reactors)", Transactions of the Japan Society of Mechanical Engineers, vol. 66, No. 646B, 2000, pp. 1501-1506 (with English translation & cited in the specification).

* cited by examiner

FIG. 2

AIR PURIFICATION SYSTEM AND PROTECTIVE CLOTHING

TECHNICAL FIELD

The present disclosure relates to an air purification system and protective clothing that includes the air purification system.

BACKGROUND ART

In the past, a processing apparatus that uses high-voltage plasma in the atmosphere for oxidation processing on NO in exhaust gases discharged from engines and other internal combustion engines has been proposed.

To generate high-voltage plasma, in the case of utilizing a voltage conversion transformer often used in a low frequency band of 10 MHz or less, it is necessary to reduce the inductance (reactance) at high frequencies greater than or equal to 100 MHz. This means that the number of coil turns and the coil size need to be reduced and the diameter of the coil used as an electric wire becomes small, thus resulting in a problem that it is not possible to input a large amount of power.

On the other hand, in the case of increasing the voltage while maintaining the characteristic impedance low at, for example, 500 without the above voltage conversion, power of 10 kW ($=1000^2 \cdot 50/2$) is necessary for a voltage of 1000 V, for instance. It is difficult in practice to provide a power source device that inputs such an amount of power.

In view of the above, Non Patent Literature (NPL) 1 below proposes a plasma reactor that generates plasma between electrodes by applying, to the electrodes, high-voltage pulses having a frequency of several kilohertz and a peak voltage in a range of from 5000 V to 10000 V for the oxidation of NO in exhaust gases discharged from engines and other internal combustion engines.

CITATION LIST

Non Patent Literature

[NPL 1] Complete NOx Removal Technology Using Nonequilibrium Plasma and Chemical Process (Performances of Ordinary and Barrier Type Plasma Reactors), Transactions of the Japan Society of Mechanical Engineers, Vol. 66, No. 646B, pp. 1501-1506 (2000)

SUMMARY OF INVENTION

Technical Problem

However, conventional air purification systems serving as plasma reactors have a problem that sufficient power is not supplied to the electrodes due to impedance mismatching of the signal of the applied pulse voltage. In addition, with high-voltage pulses of several kilohertz, the time between high-voltage pulses is longer than the electric discharge time caused by high-voltage pulses. At this time, electrons once ionized from gas recombine, and thus a large amount of energy needs to be supplied for electron ionization every time high-voltage pulses are applied. As a result, the apparatus has a low power efficiency. Therefore, even if plasma is generated, the amount of bacteria, viruses, etc. in the air decomposed by plasma is low relative to the input power.

In addition, it is difficult for conventional air purification systems to reduce: dissociation of nitrogen molecules which is, along with dissociation of oxygen molecules, induced by an intense electric field corresponding to a pulse apex value; and nitrogen oxides generated by the dissociation of nitrogen molecules. It is also difficult with the conventional technology to enable generation of ozone while preventing generation of nitrogen oxides.

In view of this, in order to address the issues described above, the present disclosure has an object to provide an air purification system and protective clothing capable of decomposing bacteria, viruses etc. in the air by efficiently generating plasma while reducing input power as compared to the conventional technology.

Solution to Problem

In order to achieve the above object, an air purification system according to an aspect of the present disclosure is an air purification system that generates plasma using voltage, the air purification system including: a first electrode that generates electromagnetic resonance when power is supplied; a second electrode disposed surrounding the first electrode in a state of being separated from the first electrode; a power feeder that supplies power to the first electrode; an electric field probe that measures an intensity of an electric field between the first electrode and the second electrode; and a controller that controls the power supplied to the first electrode, wherein the controller performs control by adjusting a frequency of the power supplied to the first electrode and a position at which the power is supplied to the first electrode, to maximize an output value of a signal indicating the intensity of the electric field measured by the electric field probe.

The air purification system further incorporates therein a detector that monitors the amounts of ozone and nitrogen oxides generated. With the amounts of ozone and nitrogen oxides generated set as targets to be controlled, the air purification system changes alternating current (AC) power, the frequency, and the power feeding point to be able to control the electric field applied to plasma so that an energy at which oxygen molecules are dissociated by plasma and ozone is thereby generated but nitrogen molecules are not dissociated and generation of nitrogen oxides is thereby minimized is inputted to gas molecules.

In order to achieve the above object, protective clothing according to an aspect of the present disclosure includes: an air purification system; and a covering body that is provided with the air purification system and covers a surface of a body of a person, and the air purification system purifies air taken in from outside and supplies purified air into the covering body.

Note that these general or specific aspects may be implemented by a system, a method, an integrated circuit, a computer program, or a computer-readable recording medium such as a compact disc read-only memory (CD-ROM), or by any combination thereof.

Advantageous Effects of Invention

According to the present disclosure, it is possible to decompose bacteria, viruses etc. in the air by efficiently generating plasma while reducing input power as compared to the conventional technology.

BRIEF DESCRIPTION OF DRAWINGS

FIG. 2 is a schematic diagram schematically illustrating, for example, the flow of air taken into the air purification system according to Embodiment 1 and changes of a power feeding point at which a power feeder supplies power to a linear electrode.

DESCRIPTION OF EMBODIMENTS

Hereinafter, embodiments according to the present disclosure are described in detail with reference to the drawings. The embodiments described below each illustrate one specific example of the present disclosure. Therefore, the numerical values, shapes, materials, constituent elements, the arrangement and connection of the constituent elements, steps, and the processing order of the steps etc. shown in the embodiments below are mere examples, and are not intended to limit the present disclosure. Accordingly, among the constituent elements included in the following embodiments, constituent elements not recited in any of the independent claims are described as optional constituent elements.

Note that the drawings are represented schematically and are not necessarily precise illustrations. In addition, in the figures, the same reference signs are given to essentially the same constituent elements, and redundant descriptions may be omitted or simplified.

Also, in the following embodiments, the term "substantially" is used. For example, the term "substantially the central portion" is intended to mean not only a portion that is exactly central, but also a portion that is essentially central, that is, including several percentages of margins of errors, for instance. Also, the term "substantially the central portion" means a central portion within a range in which advantageous effects of the present disclosure can be yielded. The same applies to other expressions including "substantial".

Hereinafter, an air purification system and protective clothing according to embodiments of the present disclosure are described.

Embodiment 1

<Configuration: Air Purification System 1>

A configuration of air purification system 1 according to the present embodiment is described.

Figure 1:
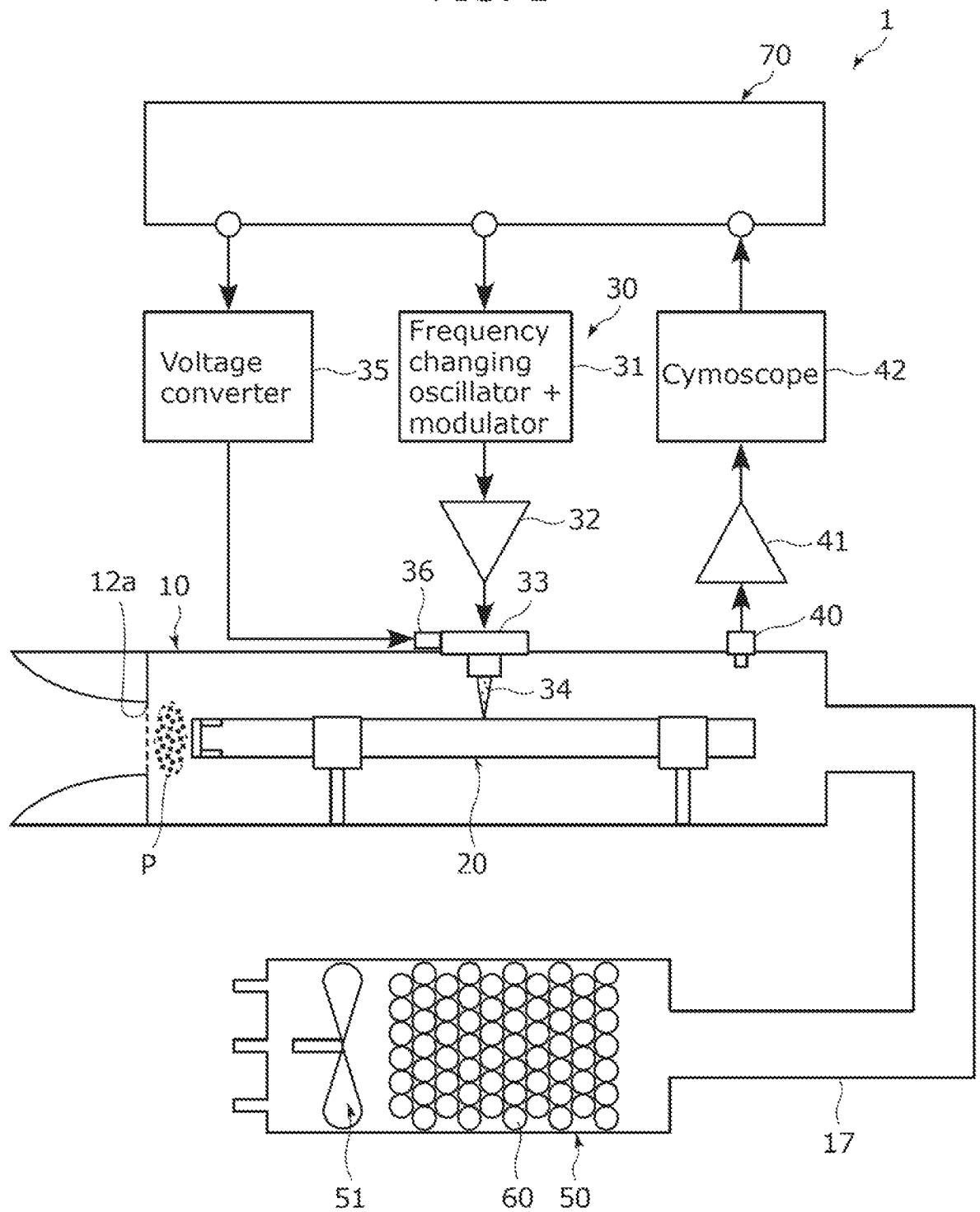
FIG. 1 is a schematic diagram illustrating an air purification system according to Embodiment 1.
Figure 2:
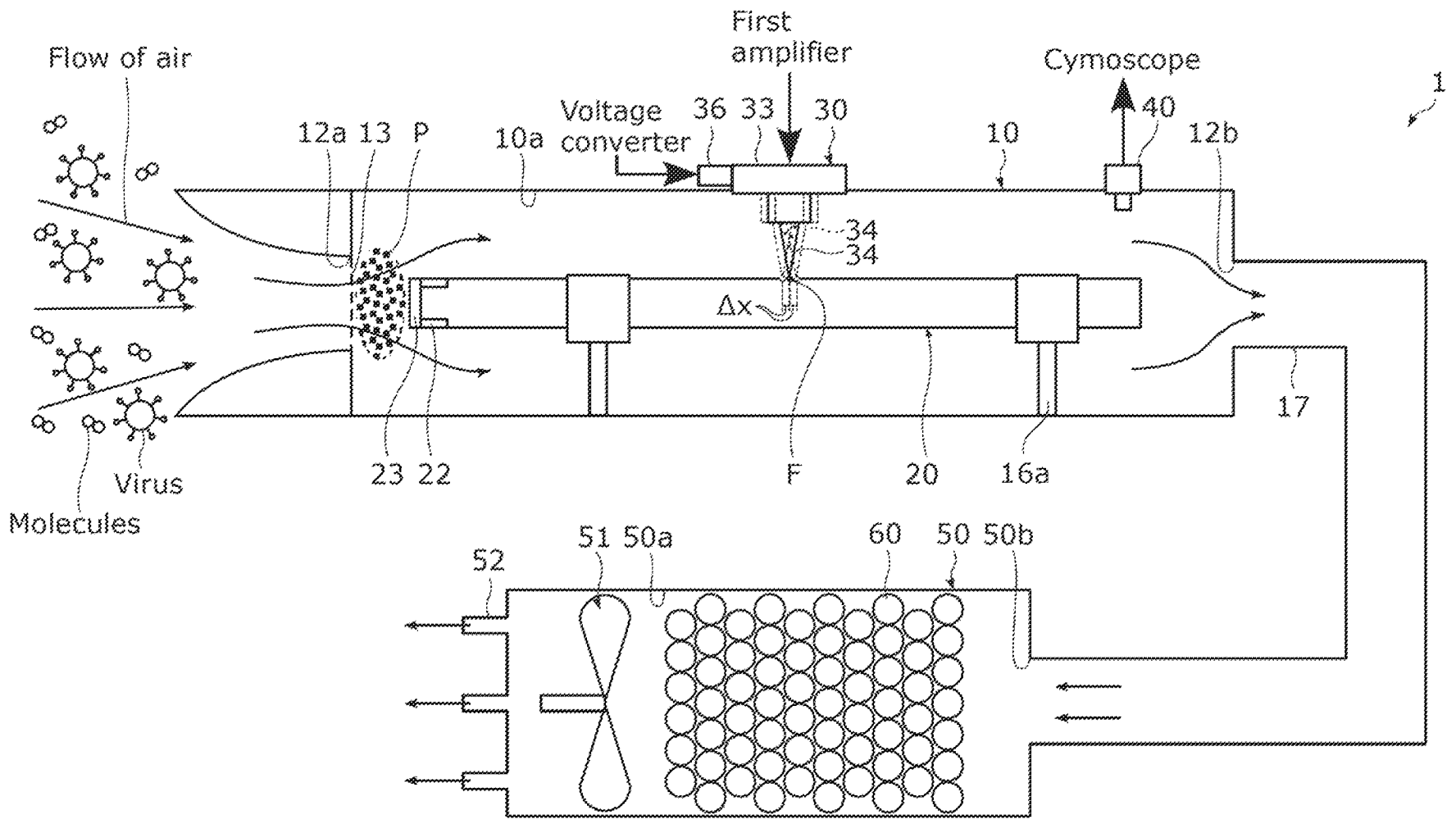

FIG. 1 is a schematic diagram illustrating air purification system 1 according to Embodiment 1. FIG. 2 is a schematic diagram schematically illustrating, for example, the flow of air taken into air purification system 1 according to Embodiment 1 and changes of power feeding point F at which power feeder 30 supplies power to linear electrode 20.

As illustrated in FIG. 1 and FIG. 2, air purification system 1 is an air purifier that decomposes, that is, kills, and removes bacteria, viruses etc., with use of a high-voltage plasma generation device capable of generating high-frequency plasma (hereinafter simply referred to as "plasma") using a high voltage in the high-frequency band. In the present embodiment, air purification system 1 generates plasma using a high voltage obtained by modulating a carrier wave having a frequency in a range of from 100 MHz to 10 GHz. Note that a high voltage is, for example, a voltage of approximately 100 V or higher. The high voltage in the present embodiment may be in a range of from $10^2$ V to $10^5$ V.

Also, the high frequency band refers to frequencies of approximately 100 MHz or higher. The high frequency band in the present embodiment may be at least 100 MHz and at most 10 GHz. The plasma in the present embodiment is atmospheric pressure plasma generated in the atmosphere at the normal pressure. Note that air purification system 1 can also decompose and remove particulates floating in the air, such as dust, pollen, mites, and smoke.

Air purification system 1 includes first housing 10, linear electrode 20, power feeder 30, electric field probe 40, second amplifier 41, cymoscope 42, voltage converter 35, actuator 36, controller 70, duct 17, second housing 50, filter 60, and fan 51.

First housing 10 forms (defines) space 10a that is elongated and accommodates linear electrode 20 in a state of being separated from linear electrode 20. First housing 10 is grounded and thus functions as a ground electrode. First housing 10 is disposed surrounding linear electrode 20 to accommodate linear electrode 20. Supports 16a for coupling linear electrode 20 are disposed and fixed in space 10a, which is the inside of first housing 10. Supports 16a are support components that separate linear electrode 20 from the inner wall surface of first housing 10 and support linear electrode 20 in a predetermined orientation. Supports 16a are formed using a material such as polytetrafluoroethylene, for example.

First housing 10 is formed using a conductive material having high electrical conductivity, such as silver, copper, or aluminum, for example. First housing 10 is an example of a second electrode.

First housing 10 is elongated in the same direction as the longitudinal direction of linear electrode 20 so as to accommodate linear electrode 20. In the present embodiment, first housing 10 is shaped according to the shape of linear electrode 20, e.g., cylindrical, but the shape of first housing 10 is not particularly limited.

First housing 10 includes inlet 12a through which air is taken in and vent 12b through which the air taken in through inlet 12a is discharged to duct 17. Inlet 12a is formed on one end side of first housing 10 in the longitudinal direction, and vent 12b is formed on the other end side of first housing 10 in the longitudinal direction. The air etc. that is present outside first housing 10 is taken in and passes through inlet 12a. Duct 17 is connected to vent 12b. The air etc. that has passed through inlet 12a and flowed through space 10a of first housing 10 passes through vent 12b and flows into duct 17.

Also, first housing 10 includes frame 13 which is like a mesh. Frame 13 is provided at inlet 12a and covers the opening surface of inlet 12a.

Linear electrode 20 is an elongated electrode which is long in a predetermined direction. Linear electrode 20 is accommodated in first housing 10 and is provided in a state of being separated from first housing 10. Specifically, linear electrode 20 is disposed in a predetermined orientation in the longitudinal direction of first housing 10 and fixed to first housing 10 via supports 16a in a state of being coupled to supports 16a to be separated from the inner wall surface of first housing 10.

Linear electrode 20 is formed using a conductive material having high electrical conductivity, such as silver, copper, or aluminum, for example. Linear electrode 20 is an example of a first electrode. Note that the first electrode may be a plate-shaped electrode and is not limited to linear electrode 20.

As illustrated in FIG. 2, modulated or unmodulated AC power supplied from power feeder 30 is applied to power feeding point F of linear electrode 20. Power feeding point F is substantially the central portion of linear electrode 20 in the longitudinal direction and is the point to which modulated or unmodulated AC power supplied from power feeder 30 is applied. According to the output value (e.g., output voltage) of a signal indicating the intensity of the electric field measured by electric field probe 40, the position of power feeding point F is changed by a predetermined distance in the longitudinal direction of linear electrode 20 from substantially the half-length position of linear electrode 20. The length of linear electrode 20 is the sum of the length of the main body of linear electrode 20 and the lengths of first dielectric 22 and second dielectric 23 in the longitudinal direction of linear electrode 20.

First dielectric 22 and second dielectric 23 are provided at an end of linear electrode 20 (an end portion closer to inlet 12a). First dielectric 22 and second dielectric 23 are provided to linear electrode 20 so as not to expose one end of linear electrode 20. First dielectric 22 is a dielectric material which is highly resistant to heat and is disposed around linear electrode 20 at one end of linear electrode 20. Second dielectric 23 is a dielectric material which is highly resistant to heat and is disposed on the end surface of one end of linear electrode 20. Each of first dielectric 22 and second dielectric 23 is, for example, ceramic such as quartz glass or alumina. In the present embodiment, first dielectric 22 is synthetic quartz and second dielectric 23 is alumina.

Linear electrode 20 generates resonance in first housing 10 when AC power is supplied from power feeder 30. AC power is supplied to linear electrode 20 to generate resonance at maximum efficiency.

Figure 3:
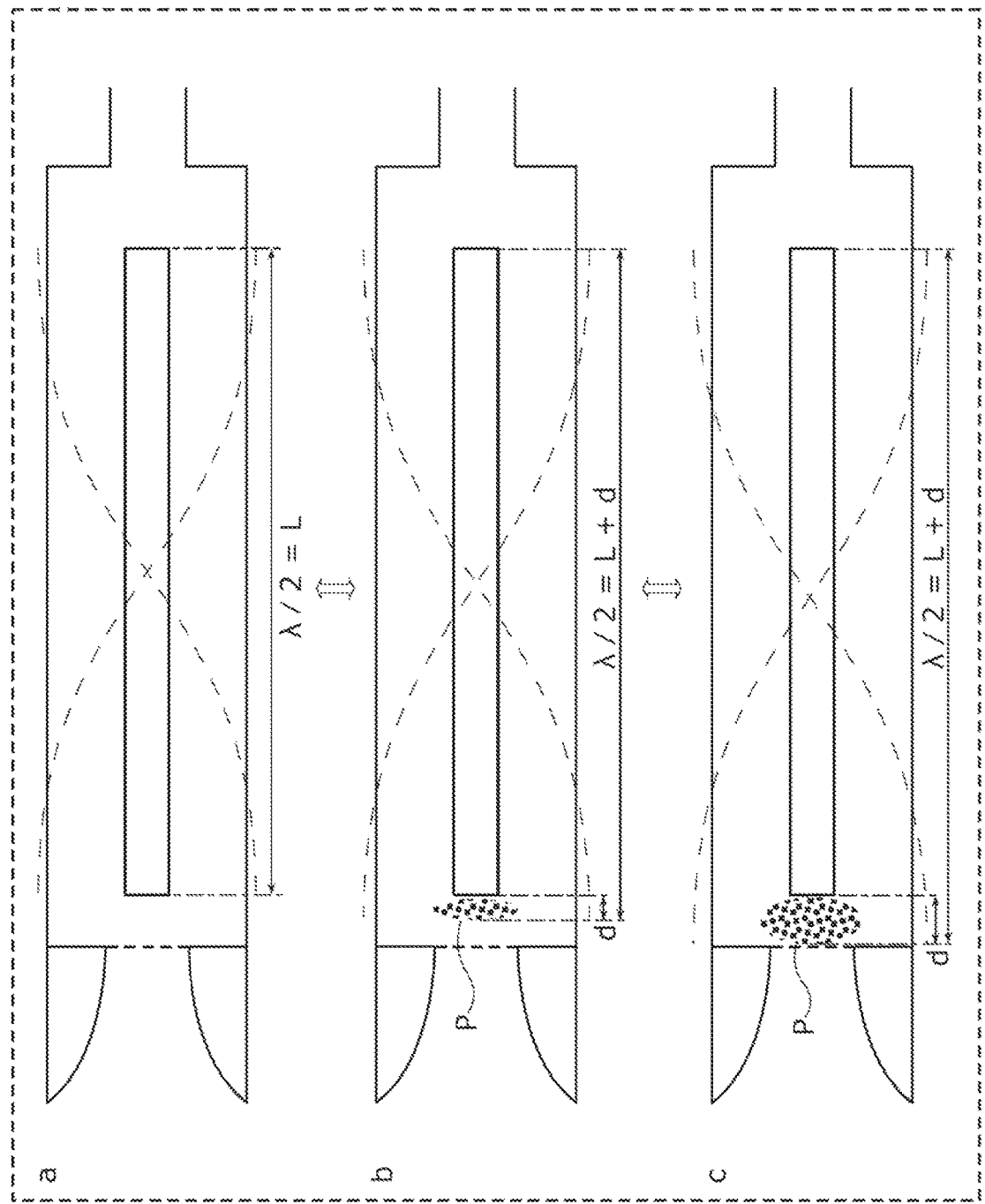
FIG. 3 is a schematic diagram illustrating changes of the length of a resonator included in the air purification system according to Embodiment 1.

FIG. 3 is a schematic diagram illustrating changes of the half wavelength during resonance in air purification system 1 according to Embodiment 1. The half wavelength during resonance in space 10a of first housing 10 represents the sum of the length of linear electrode 20 in the longitudinal direction and the length of plasma generated in plasma generation region P between one end of linear electrode 20 and inlet 12a of first housing 10 (the length in parallel to the longitudinal direction of linear electrode 20). Part a of FIG. 3 illustrates a state in which no plasma is generated in plasma generation region P. As illustrated by the dashed lines, the half wavelength of an electromagnetic wave during resonance of the electromagnetic wave in linear electrode 20 is the length of linear electrode 20 in the longitudinal direction. In other words, $\lambda/2=L$, where $\lambda/2$ is the half-wavelength of the electromagnetic wave during resonance of the electromagnetic wave in linear electrode 20, and L is the length of linear electrode 20. Next, part b of FIG. 3 illustrates the state in which plasma starts being generated in plasma generation region P. As illustrated by the dashed lines, the half wavelength of the electromagnetic wave during resonance of the electromagnetic wave is the sum of the length of linear electrode 20 in the longitudinal direction and the length of plasma. In other words, $\lambda/2=L+d$, where d (variable) is the length of plasma. Next, part c of FIG. 3 illustrates the state in which plasma has reached the maximum size in plasma generation region P, and illustrates the half wavelength of the electromagnetic wave during resonance, as illustrated by the dashed lines.

In the present embodiment, the length of linear electrode 20 is set to effectively generate plasma in plasma generation region P in the frequency band of from 100 MHz to 10 GHz.

Plasma generation region P is a region between one end of linear electrode 20 and the opening surface of inlet 12a, and is a region in space 10a of first housing 10 for generating plasma. A first shortest distance between one end of linear electrode 20 and the opening surface of inlet 12a in plasma generation region P is shorter than a second shortest distance between the other end of linear electrode 20 and the opening surface of vent 12b. By making the first shortest distance shorter than the second shortest distance, plasma is effectively generated in plasma generation region P. When first housing 10 is viewed in the longitudinal direction, plasma generation region P covers and overlaps the opening surface of inlet 12a. In plasma generation region P, the size of plasma generated and the projection surface area facing the opening surface change according to the AC power supplied to linear electrode 20.

As illustrated in FIG. 1 and FIG. 2, through supply, via first amplifier 32, of modulated or unmodulated AC current outputted by frequency changing oscillator+modulator 31 controlled by controller 70, power feeder 30 supplies the modulated or unmodulated AC current to power feeding point F of linear electrode 20. Power feeder 30 includes frequency changing oscillator+modulator 31, first amplifier 32, power feeding terminal 33, and power feeding line 34.

Frequency changing oscillator+modulator 31 has the functions of both a voltage control oscillator and a modulator that supply modulated AC power or unmodulated AC current to power feeding point F of linear electrode 20 via first amplifier 32. Specifically, by being controlled by controller 70 to maximize the output value of the signal measured by electric field probe 40 (or to cause the output value to reach a local maximum), frequency changing oscillator+modulator 31 controls the frequency of the AC power supplied to linear electrode 20. In other words, frequency changing oscillator+modulator 31 is controlled by controller 70 so that the phase of the current (or voltage) when supplying the AC power amplified by first amplifier 32 to power feeding point F and the phase of the current during resonance caused in space 10a of first housing 10 become the same phase (the phases are synchronized). The frequency changing oscillator+modulator outputs, to first amplifier 32, the AC current that is controlled to synchronize these phases.

First amplifier 32 amplifies the AC power outputted by frequency changing oscillator+modulator 31, and supplies the amplified AC power to power feeding point F via power feeding line 34. Although first amplifier 32 amplifies the AC power by a predetermined factor, the amount of amplification may be settable as appropriate.

Power feeding terminal 33 is a connection terminal for supplying the AC power amplified by first amplifier 32 to power feeding point F of linear electrode 20. Power feeding terminal 33 is fixed to first housing 10 to electrically connect power feeding line 34 and power feeding point F of linear electrode 20. Power feeding terminal 33 is a holder that holds power feeding line 34 against first housing 10.

Power feeding line 34 is a power line for supplying the AC power amplified by first amplifier 32 to power feeding point F of linear electrode 20. Power feeding line 34 is held by power feeding terminal 33 and can be moved, together with power feeding terminal 33, by actuator 36 in the longitudinal direction of linear electrode 20. Note that power feeding line 34 may be the only constituent element which can be moved by actuator 36 in the longitudinal direction of linear electrode 20.

Electric field probe 40 is a sensor that measures the intensity of the electric field between linear electrode 20 and first housing 10 when the amplified AC power is supplied to linear electrode 20. Electric field probe 40 measures the intensity of the electric field in space 10a of first housing 10, and outputs a measurement signal (a measured signal) whose output value is proportional to the intensity of the electric field to cymoscope 42 via second amplifier 41. As described later, electric field probe 40 outputs a measurement signal whose output value is maximized (or reaches a local maximum) by controller 70 controlling power feeder 30 and voltage converter 35.

Electric field probe 40 is fixed to first housing 10. Electric field probe 40 is disposed at a position on first housing 10 which is closer to vent 12b of first housing 10 and which faces the other end of linear electrode 20.

Second amplifier 41 amplifies the measurement signal outputted by electric field probe 40, and outputs the amplified measurement signal to cymoscope 42. Although second amplifier 41 amplifies the measurement signal by a predetermined factor, the amount of amplification may be settable as appropriate.

Cymoscope 42 obtains the measurement signal amplified by second amplifier 41, and performs detection on the measurement signal obtained. For example, cymoscope 42 performs detection on the measurement signal using a Schottky barrier diode. Cymoscope 42 outputs, to controller 70, a signal that indicates the detection result of the detection performed on the measurement signal. The signal indicating the detection result is a signal that indicates a result of monitoring the intensity of the electric field in first housing 10.

Voltage converter 35, by being controlled by controller 70, adjusts the voltage that voltage converter 35 supplies to actuator 36 based on a variable power source such as an external power source. By being controlled by controller 70 according to the detection result of the detection performed on the measurement signal by cymoscope 42, voltage converter 35 adjusts the voltage that voltage converter 35 supplies to actuator 36. In other words, voltage converter 35 drives actuator 36 by adjusting the voltage that voltage converter 35 applies to actuator 36.

Actuator 36 is coupled to power feeding terminal 33 of power feeder 30, and is driven when a voltage is applied by voltage converter 35. Actuator 36 is a piezoelectric element etc. that expands and contracts when driven by voltage application, for example. When driven by voltage application by voltage converter 35, actuator 36 moves power feeding line 34 in the longitudinal direction of linear electrode 20. In other words, by moving power feeding line 34, actuator 36 changes the position of power feeding point F at which AC power is supplied to linear electrode 20. Specifically, as illustrated in FIG. 2, actuator 36 adjusts the position of power feeding point F with respect to linear electrode 20 by moving the position of power feeding point F with respect to linear electrode 20 by distance Δx in the longitudinal direction of linear electrode 20. Given that an arbitrary reference position has been set, distance Δx is the amount of change in position with respect to the reference position, and is dependent on voltage $V_{in}1$ supplied from voltage converter 35. The reference position is, for example, the initial position in the state in which AC power is not supplied to linear electrode 20, or the position at the halflength of linear electrode 20 in the longitudinal direction.

With linear electrode 20, the equivalent electrode length changes because the average conductivity varies according to the density of plasma generated. This results in a slight movement in the position of the matching power feeding point. The higher the resonance Q factor is, the higher the efficiency of plasma generation is with respect to the input power and the higher the efficiency of virus decomposition is. However, the higher the Q factor is, the more important it becomes to control power feeding point F and the resonant frequency in accordance with this slight movement w. The present disclosure provides a solution to this problem.

Controller 70 is, for example, a microcontroller. Controller 70 controls power feeder 30 and voltage converter 35.

By controlling power feeder 30, controller 70 controls the AC power supplied to linear electrode 20. That is to say, controller 70 controls the frequency of the AC power supplied to linear electrode 20, to maximize the output value of the signal measured by electric field probe 40. Specifically, controller 70 controls the frequency of the AC power supplied to linear electrode 20, by controlling frequency changing oscillator+modulator 31 according to the detection result of the detection performed on the measurement signal by cymoscope 42. At this time, controller 70 controls frequency changing oscillator+modulator 31 so that the phase of the current (or voltage) supplied to power feeding point F and the phase of the current (or voltage) during resonance caused in space 10a of first housing 10 become the same phase.

By controlling voltage converter 35, controller 70 also controls the voltage applied to actuator 36. That is to say, controller 70 controls the position at which the AC power is supplied to linear electrode 20, to maximize the output value of the signal measured by electric field probe 40. In other words, controller 70 adjusts the position of power feeding point F by controlling actuator 36 according to the detection result of the detection performed by cymoscope 42 on the measurement signal.

In automatic control of maintaining this resonance state, the detection result of the detection performed on the measurement signal by cymoscope 42 (the detection result indicates a local maximum in the resonance state) is a control quantity, and the frequency of the power outputted from frequency changing oscillator+modulator 31 and the position of power feeding point F corresponding to the output of voltage converter 35 correspond to an adjustment quantity in this automatic control.

Controller 70 performs feedback control by adjusting the frequency of the AC power supplied to linear electrode 20 and the voltage applied to actuator 36 for adjusting the position of feeding point F, to maximize the output value of the measurement signal measured by electric field probe 40 which senses the intensity of the electric field in first housing 10.

Duct 17 is a pipe which connects space 10a of first housing 10 and space 50a of second housing 50 and through which the air taken in through inlet 12a of first housing 10 passes. One end of duct 17 is connected to vent 12b of first housing 10, and the other end of duct 17 is connected to vent 50b of second housing 50. That is to say, duct 17 guides the air flowing in space 10a of first housing 10 to space 50a of second housing 50.

Second housing 50 forms (defines) space 50a that accommodates filter 60 and fan 51. Filter 60 and fan 51 are disposed and fixed in space 50a, which is the inside of second housing 50. Second housing 50 is formed using a conductive material having high electrical conductivity, such as silver, copper, or aluminum. Second housing 50 may be an example of a component of the second electrode.

In the present embodiment, the shape of second housing 50 is an elongated cylindrical shape, for example, but is not particularly limited.

Second housing 50 includes vent 50b through which the air guided by duct 17 passes and outlets 52 through which the air that has entered through vent 50b is discharged to the outside of second housing 50. Vent 50b is formed on one end of second housing 50 in the longitudinal direction, and outlets 52 are formed on the other end of second housing 50 in the longitudinal direction. Duct 17 is connected to vent 50b. The air etc. that has passed through first housing 10 and duct 17 passes through vent 50b. Outlets 52 allow discharge, to the outside, of the air that has passed through vent 50b and then passed through filter 60 etc. in space 50a of second housing 50.

Filter 60 can remove ozone contained in the air generated by plasma generation when the air flowing from the vent 50b side to the outlets 52 side of second housing 50 (the air taken in through inlet 12a of first housing 10) passes through filter 60. Filter 60 is disposed in the vicinity of outlets 52 in space 50a of second housing 50 to remove ozone. Such filter 60 includes activated carbon.

Filter 60 can also adsorb, for example, remnants of bacteria, viruses, etc. Filter 60 adsorbs, for example, remnants of bacteria, viruses, etc. contained in the air that has passed through first housing 10 and duct 17.

Fan 51 is a blower that generates an airflow inside first housing 10, duct 17, and second housing 50 to allow intake of the air through inlet 12a of first housing 10 and discharge of the air through outlets 52 of second housing 50. Fan 51 is located in space 50a of second housing 50. In the present embodiment, fan 51 is disposed closer to outlets 52 of second housing 50 than filter 60 is. When the electric motor of fan 51 drives the propeller of fan 51 to rotate (i.e., when fan 51 is driven), the air is taken in through inlet 12a of first housing 10 and passes through space 10a of first housing 10 and the inside of duct 17 in the stated order, and then reaches space 50a of second housing 50, passes through filter 60, and is discharged through outlets 52 of second housing 50.

Note that the driving of fan 51 may be controlled by controller 70. That is to say, controller 70 may control the driving of fan 51 when controlling power feeder 30 and voltage converter 35.

<Frequency of AC Power and Position of Power Feeding Point F>

A description is given of the relationship between the frequency of the AC power supplied to power feeding point F and the position of power feeding point F at which the AC power is supplied, that maximizes the output value of the signal measured by electric field probe 40. The following expressions (1) to (3) are given, where $V_{in}1$ denotes a voltage that voltage converter 35 supplies to actuator 36; $v_1$ denotes a variable dependent on voltage $V_{in}1$; $V_{in}2$ denotes a control voltage of the frequency changing oscillator included in frequency changing oscillator+modulator 31 which corresponds to the frequency of the power supplied to power feeding point F; $v_2$ denotes a variable dependent on voltage $V_{in}2$; and $V_0$ denotes a voltage of the output signal of the cymoscope which indicates the detection result that cymoscope 42 outputs to controller 70 and which corresponds to the electric field at the electrode end.

[Math. 1]

$$v_1 = V_{in}1 \qquad \text{(Expression 1)}$$

[Math. 2]

$$v_2 = V_{in}2 \qquad \text{(Expression 2)}$$

[Math. 3]

$$g(v_1, v_2) = V_0 \qquad \text{(Expression 3)}$$

Using Expressions 1 through 3 above, function $g(v_1, v_2)$ that maximizes the output value of the signal measured by electric field probe 40 is calculated. In other words, the maximum value of $g(v_1, v_2)$ is calculated.

Satisfying Expressions 4 and 5 below is a condition for maximizing the electric field. On the basis of $g(v_1, v_2)$, new functions are defined as shown in Expressions 6 and 7.

[Math. 4]

$$\frac{\partial}{\partial v_1} g(v_1, v_2) = 0 \qquad \text{(Expression 4)}$$

[Math. 5]

$$\frac{\partial}{\partial v_2} g(v_1, v_2) = 0 \qquad \text{(Expression 5)}$$

[Math. 6]

-continued $$g_1(v_1, v_2) = \frac{\partial}{\partial v_1} g(v_1, v_2) \quad \text{(Expression 6)}$$

[Math. 7]

$$g_2(v_1, v_2) = \frac{\partial}{\partial v_2} g(v_1, v_2) \quad \text{(Expression 7)}$$

Calculation, using Expressions 6 and 7, of point $(v_1, v_2)$ at which each of $g_1(v_1, v_2)$ and $g_2(v_1, v_2)$ becomes 0 is expressed as Expressions 8 and 9 below.

[Math. 8]

$$g_1(v_1^{n+1}, v_2^{n+1}) = g_1(v_1^n, v_2^n) + \frac{\partial g_1(v_1^n, v_2^n)}{\partial v_1}(v_1^{n+1} - v_1^n) + \frac{\partial g_1(v_1^n, v_2^n)}{\partial v_2}(v_2^{n+1} - v_2^n) + \sigma(v^2) \quad \text{(Expression 8)}$$

[Math. 9]

$$g_2(v_1^{n+1}, v_2^{n+1}) = g_2(v_1^n, v_2^n) + \frac{\partial g_2(v_1^n, v_2^n)}{\partial v_1}(v_1^{n+1} - v_1^n) + \frac{\partial g_2(v_1^n, v_2^n)}{\partial v_2}(v_2^{n+1} - v_2^n) + \sigma(v^2) \quad \text{(Expression 9)}$$

In Expressions 8 and 9, assume $$g_1(v_1^{n+1}, v_2^{n+1}) = 0 \quad \text{[Math. 10]}$$

and $$g_2(v_1^{n+1}, v_2^{n+1}) = 0, \quad \text{[Math. 11]}$$

and ignore $$\sigma(v_2). \quad \text{[Math. 12]}$$

Then, Expressions 10 and 11 in which $$(v_1^{n+1}, v_2^{n+2}) \quad \text{[Math. 13]}$$

and $$(v_1^n, v_2^n) \quad \text{[Math. 14]}$$

are used are expressed as below.

[Math. 15]

$$\frac{\partial g_1(v_1^n, v_2^n)}{\partial v_1}(v_1^{n+1} - v_1^n) + \frac{\partial g_1(v_1^n, v_2^n)}{\partial v_2}(v_2^{n+1} - v_2^n) = -g_1(v_1^n, v_2^n) \quad \text{(Expression 10)}$$

[Math. 16]

$$\frac{\partial g_2(v_1^n, v_2^n)}{\partial v_1}(v_1^{n+1} - v_1^n) + \frac{\partial g_2(v_1^n, v_2^n)}{\partial v_2}(v_2^{n+1} - v_2^n) = -g_2(v_1^n, v_2^n) \quad \text{(Expression 11)}$$

(Expression 11)
Solving Expressions 10 and 11 leads to Expressions 12 and 13.

[Math. 17]

$$v_1^{n+1} = v_1^n - \frac{\begin{vmatrix} g_1(v_1^n, v_2^n) & \frac{\partial g_1(v_1^n, v_2^n)}{\partial v_2} \\ g_2(v_1^n, v_2^n) & \frac{\partial g_2(v_1^n, v_2^n)}{\partial v_2} \end{vmatrix}}{\begin{vmatrix} \frac{\partial g_1(v_1^n, v_2^n)}{\partial v_1} & \frac{\partial g_1(v_1^n, v_2^n)}{\partial v_2} \\ \frac{\partial g_2(v_1^n, v_2^n)}{\partial v_1} & \frac{\partial g_2(v_1^n, v_2^n)}{\partial v_2} \end{vmatrix}} \quad \text{(Expression 12)}$$

[Math. 18]

$$v_2^{n+1} = v_2^n - \frac{\begin{vmatrix} \frac{\partial g_1(v_1^n, v_2^n)}{\partial v_2} & g_1(v_1^n, v_2^n) \\ \frac{\partial g_2(v_1^n, v_2^n)}{\partial v_2} & g_2(v_1^n, v_2^n) \end{vmatrix}}{\begin{vmatrix} \frac{\partial g_1(v_1^n, v_2^n)}{\partial v_1} & \frac{\partial g_1(v_1^n, v_2^n)}{\partial v_2} \\ \frac{\partial g_2(v_1^n, v_2^n)}{\partial v_1} & \frac{\partial g_2(v_1^n, v_2^n)}{\partial v_2} \end{vmatrix}} \quad \text{(Expression 13)}$$

<Operations>

Operations of air purification system 1 according to the present embodiment are described.

As illustrated in FIG. 1 and FIG. 2, when air purification system 1 is driven, controller 70 controls the driving of power feeder 30 and voltage converter 35. At this time, controller 70 may drive fan 51 along with power feeder 30 and voltage converter 35.

By controlling power feeder 30, controller 70 causes generation of plasma in plasma generation region P. When the rotation of fan 51 causes intake of, for example, the air containing bacteria, viruses, etc. through inlet 12a of first housing 10, the air passes through plasma generation region P formed between inlet 12a and linear electrode 20.

Figure 4:
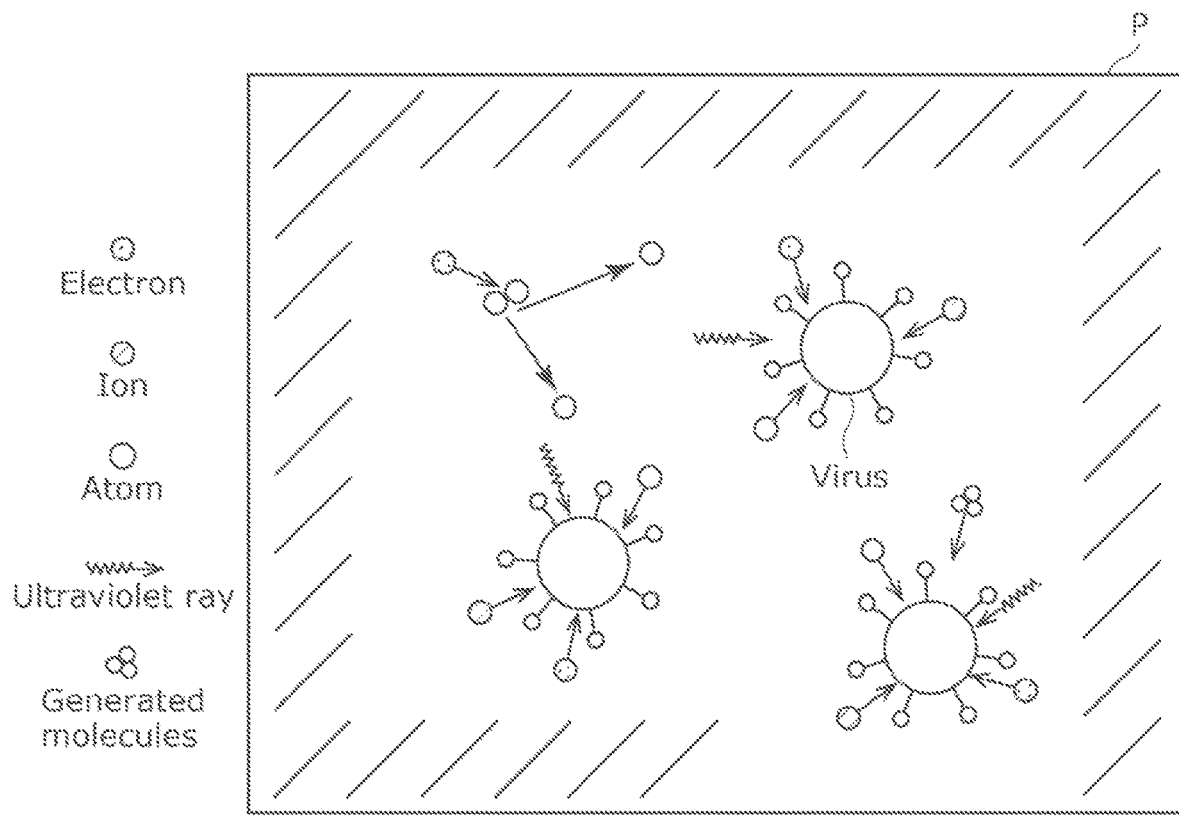
FIG. 4 is a schematic diagram illustrating how viruses are decomposed in a plasma generation region of the air purification system according to Embodiment 1.

As illustrated in FIG. 4, bacteria, viruses, etc. contained in the air are decomposed and sterilized by plasma when passing through plasma generation region P. For example, molecules, atoms, ions, electrons, etc. dissociated by plasma generation, as well as ozone and ultraviolet rays generated by plasma, collide with and decompose bacteria, viruses etc. Particulates contained in the air, such as dust, pollen, mites, and smoke are also decomposed. FIG. 4 is a schematic diagram illustrating how viruses are decomposed in plasma generation region P of air purification system 1 according to Embodiment 1.

As illustrated in FIG. 2, dust such as remnants of bacteria, viruses, etc. that have been decomposed passes through space 10a of first housing 10 together with the air, flows into second housing 50 via duct 17, and is removed from the air by being adsorbed by filter 60 of second housing 50. As a result, the air that has passed through filter 60 is purified and discharged through outlets 52 of second housing 50. In such a manner, air purification system 1 can remove, from the air, bacteria, viruses etc. contained in the air, and supply the purified air.

<Variation>

Note that as a variation of Embodiment 1, in the case of using above-described filter 60 as first filter 60, air purification system 1 may include second filter 61 different from first filter 60.

Figure 5:
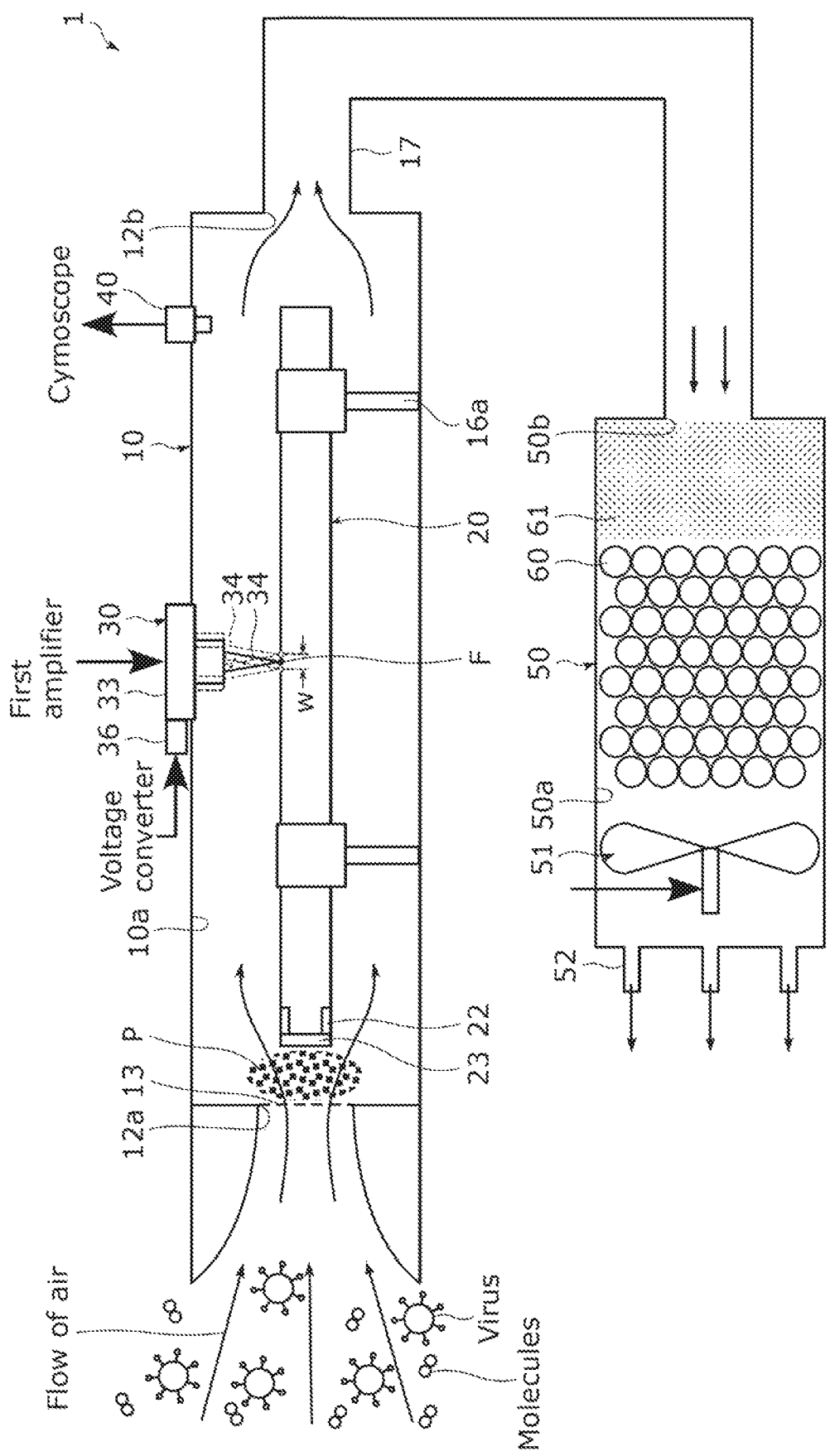
FIG. 5 is a schematic diagram schematically illustrating, for example, the flow of air taken into an air purification system according to a variation of Embodiment 1 and changes of a power feeding point at which a power feeder supplies power to a linear electrode.

FIG. 5 is a schematic diagram schematically illustrating, for example, the flow of air taken into air purification system 1 according to the variation of Embodiment 1 and changes of power feeding point F at which power feeder 30 supplies power to linear electrode 20.

As illustrated in FIG. 5, second filter 61 is disposed between first filter 60 and vent 50b of second housing 50. In other words, second filter 61 is disposed upstream of first filter 60 in the air flow. Second filter 61 is, for example, an $NO_2$ filter.

Advantageous Effects

Advantageous effects of air purification system 1 according to the present embodiment are described.

As described above, air purification system 1 according to the present embodiment is air purification system 1 that generates plasma using voltage, and includes: linear electrode 20 that generates electromagnetic resonance when AC power is supplied; first housing 10 disposed surrounding linear electrode 20 in a state of being separated from linear electrode 20; power feeder 30 that supplies AC power to linear electrode 20; electric field probe 40 that measures the intensity of an electric field between linear electrode 20 and first housing 10; and controller 70 that controls the AC power supplied to linear electrode 20. Controller 70 performs control by adjusting the frequency of the power supplied to linear electrode 20 and the position at which the power is supplied to linear electrode 20, to maximize the output value of a signal indicating the intensity of the electric field measured by electric field probe 40.

With this, it is possible to generate plasma between linear electrode 20 and first housing 10 by supplying AC power to linear electrode 20. Controller 70 controls the frequency of the AC power and the position at which the AC power is supplied to linear electrode 20. Therefore, the AC power can be synchronized with (follow) a change in the resonance frequency caused by plasma generation so that the phase of the current when supplying the AC power to linear electrode 20 and the phase of the current during resonance caused in linear electrode 20 become the same phase. At this time, since the AC power synchronized with a change in the resonance frequency can be supplied to linear electrode 20, it is possible to perform control that allows maintaining an electromagnetic resonance state at all times and allows maximizing at all times the output value of the signal measured by electric field probe 40.

Accordingly, air purification system 1 can decompose bacteria, viruses etc. contained in the air by efficiently generating plasma while reducing input power as compared to the conventional technology.

In particular, since air purification system 1 can reduce the input power, creation of a high-voltage circuit, a step-up transformer, etc., is less likely to be difficult, and power feeder 30, which is the power source of air purification system 1, does not become greater in size. Air purification system 1 can also reduce heat generation in power feeder 30 caused by an increase in the current value and reduce damages and the like of the electrodes caused by heat generation. Therefore, the manufacturing cost of air purification system 1 does not rise.

Note that air purification system 1 may be designed to increase the Q factor of resonance, in which case the AC power inputted to linear electrode 20 can be reduced.

Note that there are also methods for removing bacteria, viruses, etc. by chemical means using, for example, peracetic acid, hydrogen peroxide, ethylene oxide gas, or ozone; however, there are concerns about their impacts on the human body. In addition, there are also methods for removing bacteria, viruses, etc. by physical means such as high-pressure steam, radiation, and ultraviolet rays; however, these methods are not realistic in terms of, for example, their impacts on the human body, restrictions on usage conditions, and low energy efficiency. In contrast, air purification system 1 according to the present embodiment can remove bacteria, viruses, etc. more inexpensively and effectively than the conventional technology.

Air purification system 1 according to the present embodiment includes actuator 36 that changes the position of power feeding point F at which power feeder 30 supplies the AC power to linear electrode 20. Controller 70 adjusts the position of power feeding point F by controlling actuator 36.

With this, controller 70 can change the position of power feeding point F to maximize the output value of the signal measured by electric field probe 40. Therefore, with air purification system 1, the AC power can easily follow a change in the resonance frequency in electromagnetic resonance caused by plasma generation.

In air purification system 1 according to the present embodiment, controller 70 controls actuator 36 and power feeder 30 by controlling two parameters, namely the frequency and the position of power feeding point F on linear electrode 20, to cause the output voltage of electric field probe 40 to reach a local maximum. In other words, controller 70 performs feedback control by adjusting the frequency and the position of power feeding point F on linear electrode 20, to cause the output voltage of electric field probe 40 to reach a local maximum.

With this, since the resonance can be maintained, plasma can be efficiently generated while more reliably reducing the input power.

In air purification system 1 according to the present embodiment, first housing 10 is a housing including inlet 12a through which the air is taken in. Air purification system 1 includes filter 60 that is disposed in the vicinity of outlets 52 through which the air taken in through inlet 12a is discharged, and that, when the air taken in through inlet 12a passes through, removes nitrogen oxides and ozone generated by a plasma reactor including linear electrode 20 and first housing 10.

With this, it is possible to supply purified air from which dust such as remnants of bacteria and viruses, etc., decomposed by plasma has been removed.

In air purification system 1 according to the present embodiment, linear electrode 20 is an elongated electrode. First housing 10 forms, in the longitudinal direction of linear electrode 20, space 10a that is elongated and accommodates linear electrode 20. In space 10a, plasma generation region P for generating plasma is provided between linear electrode 20 and inlet 12a of first housing 10.

With this, since plasma generation region P is provided in the vicinity of inlet 12a, it is possible to ensure that the air passing through inlet 12a passes through plasma generation region P. Therefore, bacteria, viruses, etc. contained in the air can be reliably decomposed.

Embodiment 2

Air purification system 2a according to the present embodiment is described.

The present embodiment is different from Embodiment 1 in that air purification system 2a according to the present embodiment further includes second filter unit 101, heater 102, third filter unit 103, and first detector 105a. A configuration of main body 1a in air purification system 2a according to the present embodiment is the same as the configuration of the air purification system according to Embodiment 1, and the same reference signs are given to the same constituent elements and detailed descriptions thereof are omitted. In the present embodiment, air purification system 1 according to Embodiment 1 is referred to as main body 1a.

Figure 6:
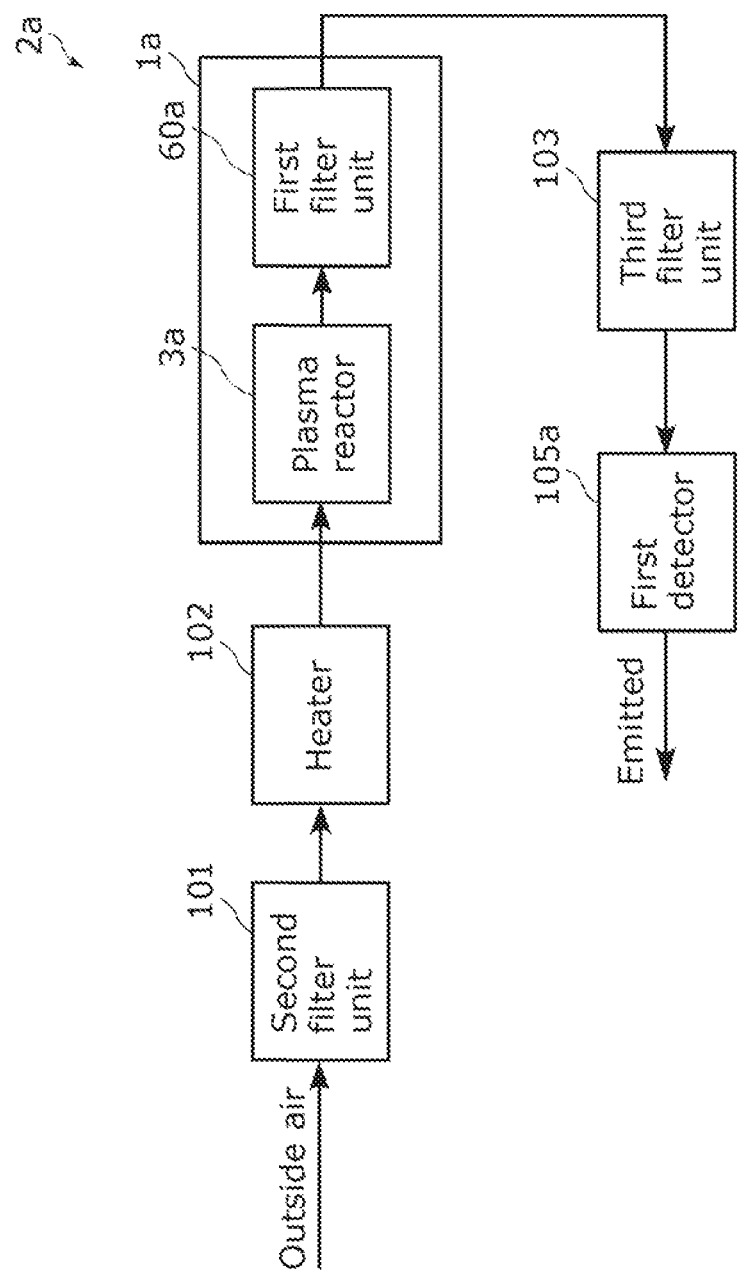
FIG. 6 is a block diagram illustrating an air purification system according to Embodiment 2 which includes, for example, a flow control valve having a flow meter.
Figure 7:
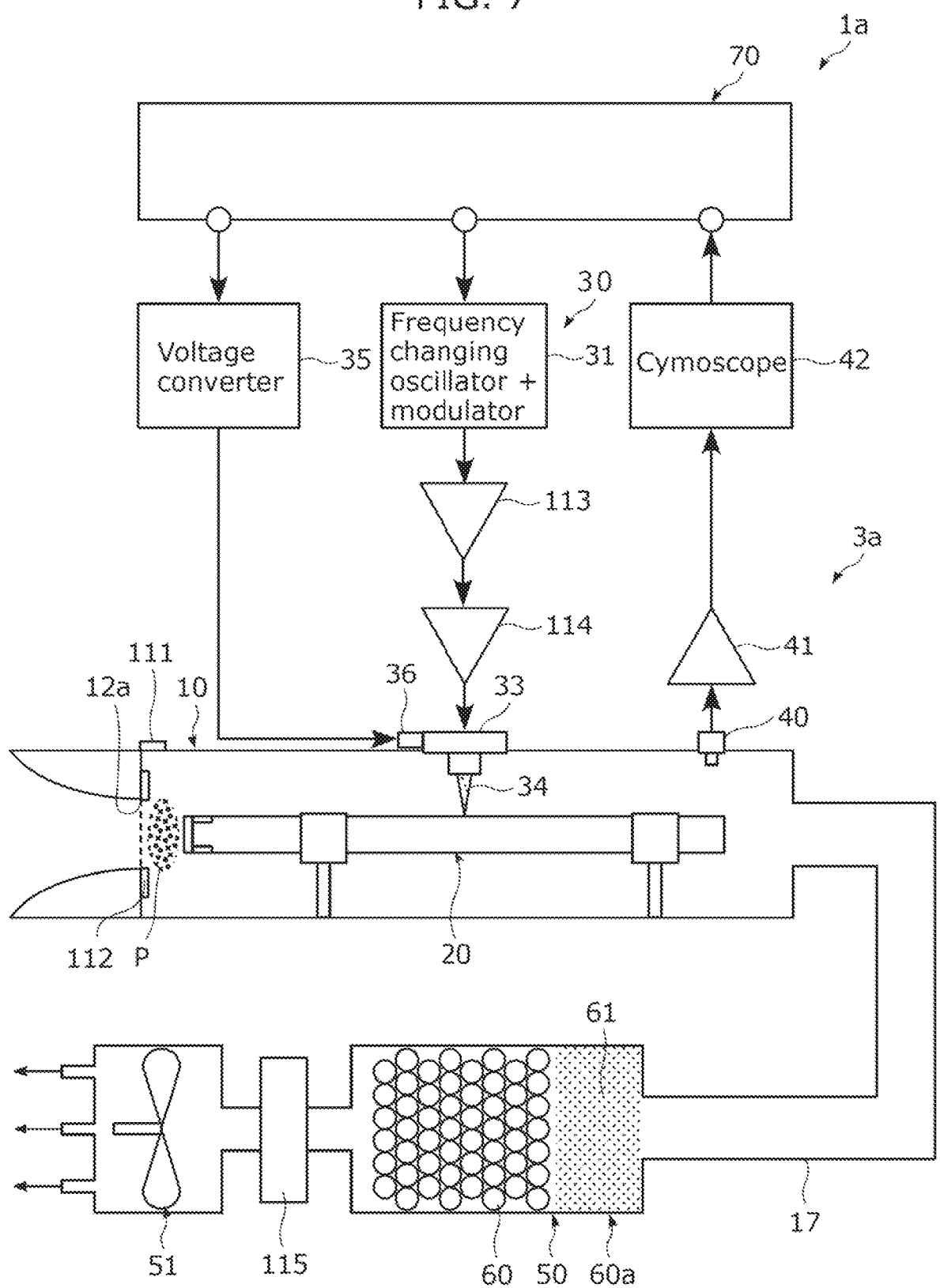
FIG. 7 is a schematic diagram illustrating a main body of the air purification system according to Embodiment 2.

FIG. 6 is a block diagram illustrating air purification system 2a according to Embodiment 2 which further includes, for example, flow control valve 115 having a flow meter. FIG. 7 is a schematic diagram illustrating main body 1a of air purification system 2a according to Embodiment 2.

As illustrated in FIG. 6 and FIG. 7, air purification system 2a includes main body 1a, second filter unit 101, heater 102, third filter unit 103, and first detector 105a.

Main body 1a Includes plasma reactor 3a and first filter unit 60a.

Plasma reactor 3a includes spectroscope 111 and third dielectric 112, as well as first housing 10, linear electrode 20, electric field probe 40, actuator 36, power feeding terminal 33, and power feeding line 34. Note that plasma reactor 3a may selectively include one or more of the following constituent elements: frequency changing oscillator+modulator 31, first amplifier 113, second amplifier 114, second amplifier 41, cymoscope 42, voltage converter 35, controller 70, and duct 17.

Note that in the present embodiment, air purification system 2a includes, instead of the first amplifier of Embodiment 1, first amplifier 113 and second amplifier 114. First amplifier 113 is, for example, an operational amplifier that converts impedance, and second amplifier 114 is, for example, a power amplifier. First amplifier 113 and second amplifier 114 are included in the configuration of power feeder 30.

Spectroscope 111 is disposed on the inlet 12a side of first housing 10. Specifically, spectroscope 111 is fixed to the outer surface of first housing 10, on the inlet 12a side of first housing 10. Spectroscope 111 detects the emission intensity of plasma in plasma generation region P. Note that spectroscope 111 may output the detection result to controller 70, and controller 70 may adjust the frequency (frequency changing oscillator+modulator 31) and the position of the power feeding point (the output voltage of the voltage converter) according to the detection result.

Third dielectric 112 is disposed in space 10a of first housing 10. Specifically, third dielectric 112 is disposed in the vicinity of inlet 12a to surround or interpose inlet 12a of first housing 10. Third dielectric 112 is disposed also in the vicinity of second dielectric 23 disposed at one end of linear electrode 20. Third dielectric 112 is a dielectric material that is highly resistant to heat. Third dielectric 112 is, for example, ceramic such as quartz glass or alumina.

First filter unit 60a includes second housing 50, first filter 60, second filter 61, fan 51, and flow control valve 115 having a flow meter. Note that first filter unit 60a may include duct 17. Although activated carbon is used for first filter 60 in the present embodiment, ammonia may be used instead of activated carbon to catalytically decompose nitrogen oxides.

Flow control valve 115 having a flow meter is disposed between fan 51 and first filter 60. That is to say, flow control valve 115 having a flow meter measures and controls the flow rate of the air that flows from first filter 60 to fan 51 and has passed through first filter 60.

Before the air is taken in as outside air through inlet 12a of first housing 10 included in plasma reactor 3a, second filter unit 101 filters such air. That is to say, second filter unit 101 is an air filter disposed upstream of plasma reactor 3a. Second filter unit 101 removes suspended particulates contained in the air before taken into plasma reactor 3a. Suspended particulates include not only bacteria and viruses but also particulates such as dust, pollen, mites, and smoke. Second filter unit 101 is, for example, activated carbon, a photocatalyst, a high efficiency particulate air (HEPA) filter, an ultra low penetration air (ULPA) filter, a medium efficiency particulate air (MEPA) filter, etc. The air which has passed through second filter unit 101 and from which suspended particulates have been removed, flows into heater 102.

By adjusting the amount of moisture contained in the air that has passed through second filter unit 101, heater 102 adjusts the amount of moisture (humidity) of the air flowing into plasma reactor 3a of main body 1a. Heater 102 includes a humidity control heater for adjusting the humidity of the air that passes through heater 102 and a mist separator that separates, from the air, moisture contained in the air. The air which has passed through heater 102 and whose humidity has been adjusted flows into plasma reactor 3a.

Plasma reactor 3a decomposes bacteria, viruses, etc. contained in the air that has flowed into plasma reactor 3a from heater 102. The AC power controlled by controller 70 is supplied to plasma reactor 3a so that, by plasma, an energy which is intermediate between the dissociation energy of oxygen molecules contained in the air (approximately 5 eV) and the dissociation energy of nitrogen molecules (approximately 9 eV) is applied to gas molecules and only the oxygen molecules are thereby dissociated. The air that has passed through plasma reactor 3a is filtered by first filter unit 60a and flows into third filter unit 103.

Third filter unit 103 filters the air that has passed through plasma reactor 3a and first filter unit 60a. That is to say, third filter unit 103 is an air filter disposed downstream of plasma reactor 3a. Third filter unit 103 removes dust contained in the air that has passed through plasma reactor 3a. Third filter unit 103 is, for example, activated carbon, a photocatalyst, an HEPA filter, a ULPA filter, an MEPA filter, etc. The air which has passed through third filter unit 103 and from which dust has been removed (purified air) flows into first detector 105a.

First detector 105a detects and measures the contents of ozone and nitrogen oxides contained in the air that has been generated through plasma generation and purified. First detector 105a outputs, to controller 70, the measurement result of the contents of ozone and nitrogen oxides contained in the purified air. First detector 105a is an example of a detector.

On the basis of the measurement result of the contents of ozone and nitrogen oxides contained in the air measured by first detector 105a, controller 70 adjusts the power supplied to linear electrode 20 by operating frequency changing oscillator+modulator 31 and amplifier 32, in order to perform control to (i) cause the amount of ozone generated due to plasma generation to become constant at all times, and (ii) apply an energy having an intermediate value between the dissociation energy of oxygen molecules and the dissociation energy of nitrogen molecules, at which nitrogen oxides are substantially not generated. This control may be feedback control which includes this operation and adjustment. When the measurement result shows contents of ozone and nitrogen oxides exceeding predetermined values, controller 70 performs control to temporarily stop air purification system 2a so as to prevent discharge of the purified air from air purification system 2a.

In order to perform control to cause the amount of ozone to become constant at all times, controller 70 performs such operations as follows via frequency changing oscillator+modulator 31 on the basis of the measurement result from, for example, first detector 105a: adjustment of the amplitude of the AC power supplied to linear electrode 20; amplitude modulation on the AC power; and adjustment of the amplitude modulation to cause the value of the amplitude modulation to intermittently repeat a given value and zero. This control may be feedback control. For example, controller 70 controls the amount of plasma generated, by adjusting the duty cycle of the AC power through amplitude modulation.

By doing so, it is possible to control the contents of ozone and nitrogen oxides contained in the purified air.

When controller 70 performs amplitude modulation via frequency changing oscillator+modulator 31, the waveform of the AC power supplied to linear electrode 20 is a waveform obtained by performing the amplitude modulation on a carrier wave. At this time, controller 70 adjusts the power supplied to linear electrode 20 via frequency changing oscillator+modulator 31, to perform control to cause the amount of ozone to be, for example, less than or equal to the amount of ozone originally contained in the earth's atmosphere, and preferably, to cause the ozone concentration to be less than or equal to 0.1 ppm. This control may be feedback control.

Advantageous Effects

Advantageous effects of air purification system 2a according to the present embodiment are described.

For example, with conventional air purification systems, it is difficult to control dissociation of nitrogen molecules induced by an intense electric field corresponding to a pulse apex value and to control the nitrogen oxides generated as a result.

In view of this, air purification system 2a according to the present embodiment includes first detector 105a that monitors the amounts of ozone and nitrogen oxides generated. With the amounts of ozone and nitrogen oxides generated set as targets to be controlled, air purification system 2a, for example, adjusts the waveform of the input power, adjusts the amplitude modulation, and adjusts the electric field applied to plasma while maintaining electromagnetic resonance so that an energy at which oxygen molecules are dissociated by plasma and ozone is thereby generated but nitrogen molecules are not dissociated and generation of nitrogen oxides is thereby minimized is inputted to gas molecules. As a result, it is possible to prevent discharge of harmful gas and perform safe and highly efficient air purification. Control corresponding to these adjustments may be feedback control.

As described, in air purification system 2a according to the present embodiment, controller 70 obtains from first detector 105a the measurement result of the content of ozone contained in the air that has passed through the region between linear electrode 20 and first housing 10 (or plasma generation region P), and on the basis of the measurement result obtained, adjusts the power supplied, for controlling the air passing through the region between linear electrode 20 and first housing 10 to (i) cause the amount of ozone generated due to plasma generation to become constant at all times, and (ii) apply an energy having an intermediate value between the dissociation energy of oxygen molecules and the dissociation energy of nitrogen molecules, at which nitrogen oxides are substantially not generated. This adjustment may be feedback control.

With this, plasma reactor 3a can efficiently generate the minimum ozone necessary for decomposition of viruses, cause the concentration of ozone contained in the purified air to be a concentration harmless to the human body and so on, kill the bacteria and viruses contained in the air, and easily remove the generated ozone using filter 60.

In air purification system 2a according to the present embodiment, the power supplied to linear electrode 20 is AC power. Controller 70 performs control to cause the amount of ozone generated to become constant at all times. Controller 70 adjusts the amplitude of the AC power supplied, so as to cause the amount of ozone generated to be less than or equal to the amount of ozone originally contained in the earth's atmosphere, for example. This control may be feedback control.

In this case, too, it is possible to cause the concentration of ozone contained in the purified air to be a concentration harmless to the human body and so on; for example, cause the amount of ozone to be less than or equal to the amount of ozone originally contained in the earth's atmosphere, and it is also possible to kill the bacteria and viruses contained in the air and easily remove the generated ozone using filter 60.

In air purification system 2a according to the present embodiment, the waveform of the AC power supplied to linear electrode 20 is a waveform obtained by performing amplitude modulation on a carrier wave. Controller 70 performs control by adjusting the amplitude modulation to cause the amount of ozone generated to become constant; for example, cause the amount of ozone generated to be less than or equal to the amount of ozone originally contained in the earth's atmosphere. This control may be feedback control.

In this case, too, it is possible to cause the concentration of ozone contained in the purified air to be a concentration harmless to the human body and so on; for example, cause the amount of ozone to be less than or equal to the amount of ozone originally contained in the earth's atmosphere, and it is also possible to kill the bacteria and viruses contained in the air and easily remove the generated ozone using filter 60.

In air purification system 2a according to the present embodiment, the waveform of the AC power supplied to linear electrode 20 is a waveform obtained by performing amplitude modulation on a carrier wave. Controller 70 performs control to cause the amount of ozone generated to become constant. For example, in order to perform control to cause the amount of ozone to be less than or equal to the amount of ozone originally contained in the earth's atmosphere, the time interval is adjusted to cause the value of the amplitude modulation to intermittently repeat a given value and zero. This control may be feedback control.

In this case, too, it is possible to cause the concentration of ozone contained in the purified air to be a concentration harmless to the human body and so on; for example, to cause the amount of ozone to be less than or equal to the amount of ozone originally contained in the earth's atmosphere, and it is also possible to kill the bacteria and viruses contained in the air and easily remove the generated ozone using filter 60.

Also, in air purification system 2a according to the present embodiment, controller 70 adjusts the power supplied, for the purpose of performing control to cause the ozone concentration to be less than or equal to 0.1 ppm. This control may be feedback control.

In this case, too, it is possible to cause the concentration of ozone contained in the purified air to be a concentration harmless to the human body and so on; for example, to cause the amount of ozone to be less than or equal to the amount of ozone originally contained in the earth's atmosphere, and it is also possible to kill the bacteria and viruses contained in the air and easily remove the generated ozone using filter 60.

Also, air purification system 2a according to the present embodiment generates plasma using a high voltage having a continuous wave of a frequency in a range of from 100 MHz to 10 GHz obtained by performing frequency modulation.

In air purification system 2a, the Q factor becomes 1000 or greater, and thus, the inputted high-frequency voltage can be boosted precisely by 1000 times or more. In this case, since the power is supplied from first amplifier 32 to linear electrode 20 of air purification system 2a at a power efficiency greater than or equal to 99%, the power efficiency is substantially 100%. When a high voltage having a high frequency in a range of from 10 MHz to 10 GHz is supplied to linear electrode 20, the oscillation amplitude of electrons in first housing 10 is not so great and the speed of the electrons is in a limited range, and therefore, high-density plasma can be generated.

For example, the dissociation energy of nitrogen molecules is approximately 9 eV, the dissociation energy of oxygen molecules is approximately 5 eV, and the envelope breakdown energy of, for example, viruses contained in the air is approximately 5 eV or less. In air purification system 2a, an energy of approximately 5 eV or greater is applied to gas molecules so that ozone is efficiently generated by dissociating oxygen molecules while inhibiting generation of nitrogen oxides. This allows not only direct attack, i.e., inelastic collision, of ionized ions, electrons, and radicals on viruses, but also: decomposition of the viruses by efficiently generating ozone through dissociation of oxygen molecules; and inhibition of generation of harmful nitrogen oxides. In the present disclosure, feedback control is performed on a change in the resonance state caused by a change in the plasma state and the type and amount of gas molecules flowing in, so as to maintain the electromagnetic resonance state at all times by adjusting the frequency of the input power and the position of the power feeding point. By doing so, it is possible to maintain high "power-virus" decomposition efficiency. Furthermore, by adjusting the intensity (may be the average intensity) of the input power, e.g., the waveform or amplitude of the input power in the resonance state, control can be performed to cause the concentration of ozone contained in the air that is eventually discharged from the air purifier for human breathing, to be less than or equal to 0.1 ppm or about the concentration of ozone originally contained in the earth's atmosphere, while efficiently generating the minimum ozone necessary for decomposition of viruses. Control corresponding to this series of adjustments may be feedback control.

Ozone at a concentration less than or equal to 0.1 ppm can be removed by filter 60, for example. The result of detection by first detector 105a is fed back to controller 70 to apply, to gas molecules inputted to plasma reactor 3a, an energy that is greater than equal to the dissociation energy of oxygen and less than or equal to the dissociation energy of nitrogen, or an energy equivalent to the dissociation energy of oxygen. Thus, it is possible to supply, as purified air necessary for human breathing, purified air in which the generation of nitrogen oxides is inhibited while the minimum amount of ozone necessary for decomposition of bacteria, viruses, etc. is generated.

Supply of a high voltage having a high frequency to linear electrode 20 results in application of an energy which exceeds the dissociation energy of nitrogen molecules contained in the gas inputted to plasma reactor 3a. This causes generation of nitrogen oxides due to nitrogen molecules contained in the air and generation of excessive ozone for the purpose of decomposing viruses. By controlling the plasma generation (By controller 70 controlling the high-frequency AC power supplied to linear electrode 20) to cause no generation of nitrogen oxides and cause the concentration of ozone contained in the purified air to be a concentration harmless to the human body and so on (e.g., 0.1 ppm), it is possible to kill bacteria and viruses contained in the air using the minimum amount of ozone necessary, and easily remove excess ozone using filter 60.

<Variation 1>

Figure 8:
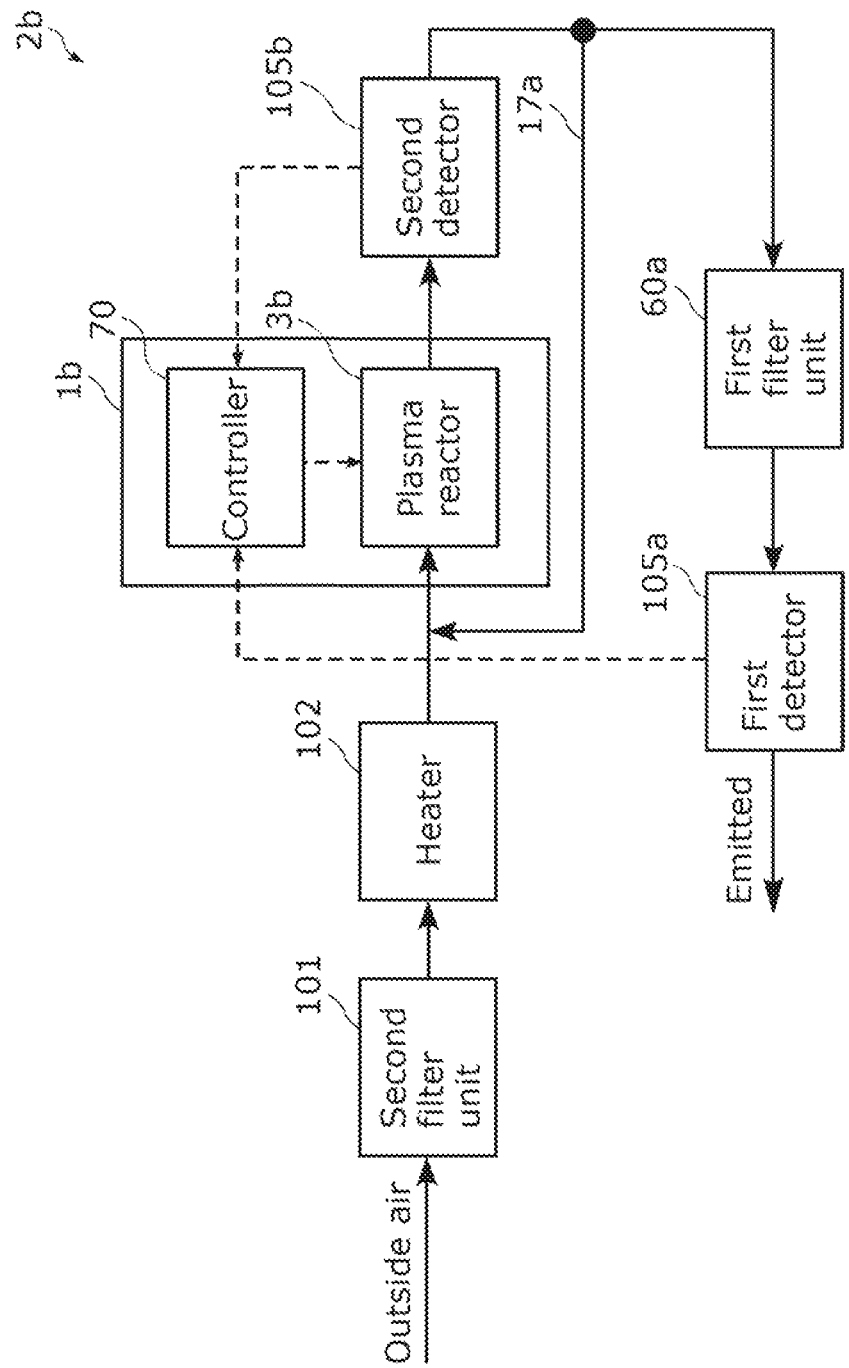
FIG. 8 is a block diagram illustrating an air purification system according to Variation 1 of Embodiment 2 which includes, for example, a second filter unit, a heater, a second detector, a first filter unit, a first detector, and a pipe.

FIG. 8 is a block diagram illustrating air purification system 2b according to Variation 1 of Embodiment 2 which includes second filter unit 101, heater 102, second detector 105b, first filter unit 60a, first detector 105a, and pipe 17a. In FIG. 8, the flow of air, as outside air, is illustrated by solid arrows, and the flow of signals such as a measurement result is illustrated by dashed arrows.

Air purification system 2b according to the present variation is different from the air purification system according to Embodiment 2 in that, for example, main body 1b includes controller 70.

Air purification system 2b according to Variation 1 of Embodiment 2 includes main body 1b, second filter unit 101, heater 102, second detector 105b, first filter unit 60a, and first detector 105a. In the present variation, air purification system 2b does not include the third filter unit included in Embodiment 2. In the present variation, first filter unit 60a is used instead of the third filter unit included in Embodiment 2.

Main body 1b includes plasma reactor 3b and controller 70. In the present embodiment, main body 1b does not include first filter unit 60a. First filter unit 60a is disposed downstream of plasma reactor 3b because the air that has passed through plasma reactor 3b flows into first filter unit 60a. Note that although main body 1b includes frequency changing oscillator+modulator 31, first amplifier 113, second amplifier 114, second amplifier 41, cymoscope 42, voltage converter 35, duct 17, second housing 50, filter 60, fan 51, and so on illustrated in FIG. 7, the configuration is simplified in FIG. 8.

Plasma reactor 3b includes first housing 10, linear electrode 20, power feeder 30, electric field probe 40, actuator 36, spectroscope 111, third dielectric 112, first amplifier 113, second amplifier 114, second amplifier 41, cymoscope 42, and voltage converter 35.

Second detector 105b is disposed between plasma reactor 3b and first filter unit 60a. The air that has passed through plasma reactor 3b passes through second detector 105b. Second detector 105b detects and measures the contents of ozone and nitrogen oxides contained in a gas which has been purified by plasma and in which bacteria, viruses, etc. have been decomposed by plasma. As with first detector 105a, second detector 105b also outputs, to controller 70, the measurement result of the contents of ozone and nitrogen oxides contained in the purified air. Second detector 105b may also be an example of the detector.

Using the measurement result of second detector 105b as the control target, controller 70 adjusts the AC power supplied from power feeder 30 to linear electrode 20 of plasma reactor 3b. This adjustment may be feedback control. When the measurement result shows contents of ozone and nitrogen oxides exceeding predetermined values, controller 70 adjusts the AC power supplied to linear electrode 20, to inhibit generation of ozone and nitrogen oxides. This adjustment may be feedback control.

Air purification system 2b according to the present variation includes pipe 17a that returns the air that has passed through second detector 105b, to plasma reactor 3b. For example, pipe 17a makes connection from the outlet side to the inlet 12a side of first housing 10 included in plasma reactor 3b. In the present embodiment, pipe 17a makes connection from a duct connecting second detector 105b and first filter unit 60a to a duct connecting heater 102 and plasma reactor 3b. Pipe 17a returns part of the air that has passed through first housing 10, to the inlet 12a side of first housing 10 for circulation. Note that pipe 17a may be provided with a fan or the like to return the air to plasma reactor 3b.

The purified gas that has passed through first filter unit 60a passes through first detector 105a.

Such air purification system 2b according to the present variation includes pipe 17a which returns, to the inlet 12a side, part of the air that has been taken in through inlet 12a and has passed through the inside of first housing 10 (plasma reactor 3b).

According to this, by returning part of the air that has passed through first housing 10, to the inlet 12a side, it is possible to ensure again that suspended matter such as bacteria and viruses is decomposed. The above-described circulation of part of the air that has passed through first housing 10 enables further purification of the air.

<Variation 2>

Figure 9:
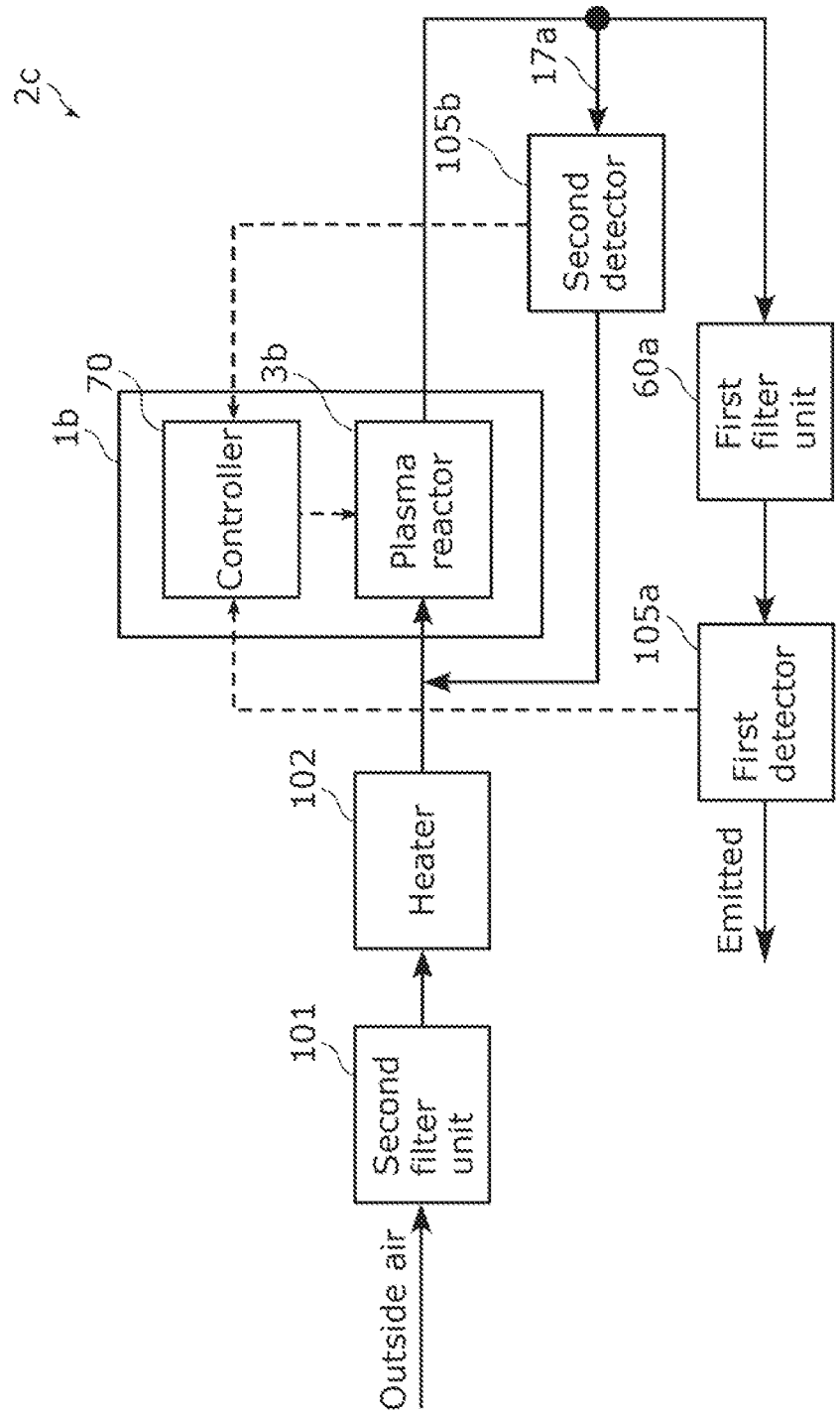
FIG. 9 is a block diagram illustrating an air purification system according to Variation 2 of Embodiment 2 which includes a second filter unit, a heater, a second detector, a pipe, a first filter unit, and a first detector, and in which the second detector is provided to the pipe.

FIG. 9 is a block diagram illustrating air purification system 2c according to Variation 2 of Embodiment 2 which includes second filter unit 101, heater 102, second detector 105b, pipe 17a, first filter unit 60a, and first detector 105a, and in which second detector 105b is provided to pipe 17a.

Air purification system 2c according to the present variation is different from the air purification system according to Variation 1 of Embodiment 2 in that second detector 105b is provided on pipe 17a.

As illustrated in FIG. 9, pipe 17a makes connection from a duct connecting plasma reactor 3b and first filter unit 60a to a duct connecting heater 102 and plasma reactor 3b. Second detector 105b is disposed on pipe 17a. Note that although main body 1b includes frequency changing oscillator+modulator 31, first amplifier 113, second amplifier 114, second amplifier 41, cymoscope 42, voltage converter 35, duct 17, second housing 50, filter 60, fan 51, and so on illustrated in FIG. 7, the configuration is simplified in FIG. 9.

First filter unit 60a is connected to plasma reactor 3b and filters the air that has passed through plasma reactor 3b.

In air purification system 2c, controller 70 adjusts the intensity or waveform (the average intensity) of the power inputted to the plasma reactor, for the purpose of applying, to molecules (e.g., $O_2$, $N_2$) contained in the air taken into air purification system 2c, an energy that is less than or equal to the dissociation energy of $N_2$ (e.g., approximately 9 eV) and is in the vicinity of the dissociation energy of $O_2$ (e.g., approximately 5 eV), in order to prevent generation of nitrogen oxides that are harmful to the human body. This adjustment may be feedback control. Controller 70 performs control to cause the output of second detector 105b disposed inside or outside plasma reactor 3b to be an amount of generated ozone of 1 ppm or less, for example.

As described, in the present variation, controller 70 adjusts the input power inputted to plasma reactor 3b, for the purpose of applying, to a gas taken into plasma reactor 3b, an energy that is greater than or equal to the dissociation energy of oxygen molecules contained in the air taken in through inlet 12a and is less than or equal to the dissociation energy of nitrogen molecules. This adjustment may be feedback control.

<Variation 3>

Figure 10:
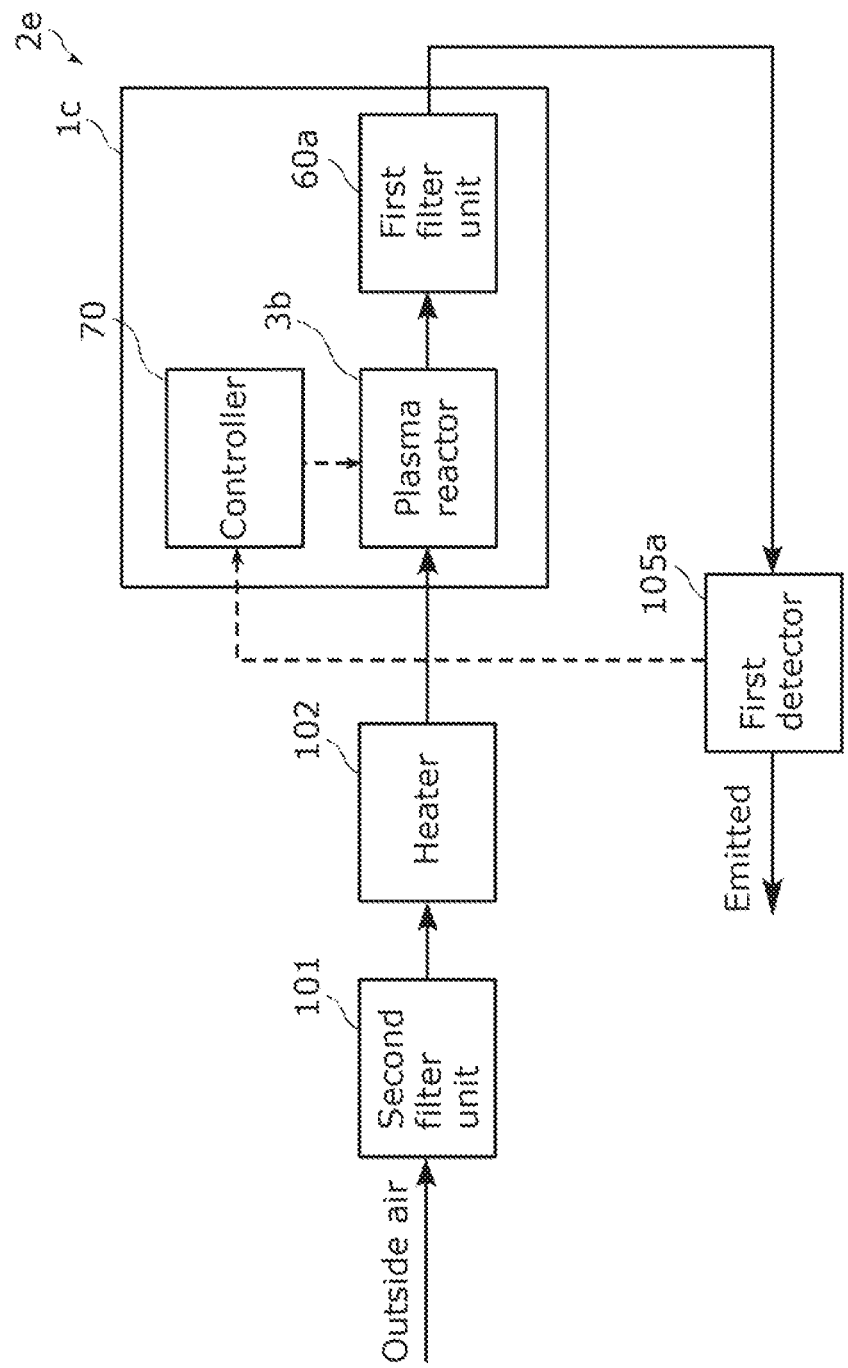
FIG. 10 is a block diagram illustrating an air purification system according to Variation 3 of Embodiment 2 which includes a second filter unit, a heater, and a first detector, and in which a main body including a controller and so on is used.

FIG. 10 is a block diagram illustrating air purification system 2e according to Variation 3 of Embodiment 2 which includes second filter unit 101, heater 102, and first detector 105a, and in which main body 1c including controller 70 and so on is used.

Air purification system 2e according to the present variation is different from the air purification system according to Variation 2 of Embodiment 2 in that the second detector and the pipe are not included and that main body 1c includes first filter unit 60a.

As illustrated in FIG. 10, main body 1c according to the present variation includes plasma reactor 3b, first filter unit 60a, and controller 70. Note that although main body 1c includes frequency changing oscillator+modulator 31, first amplifier 113, second amplifier 114, second amplifier 41, cymoscope 42, voltage converter 35, duct 17, second housing 50, filter 60, fan 51, and so on illustrated in FIG. 7, the configuration is simplified in FIG. 10.

<Variation 4>

Figure 11:
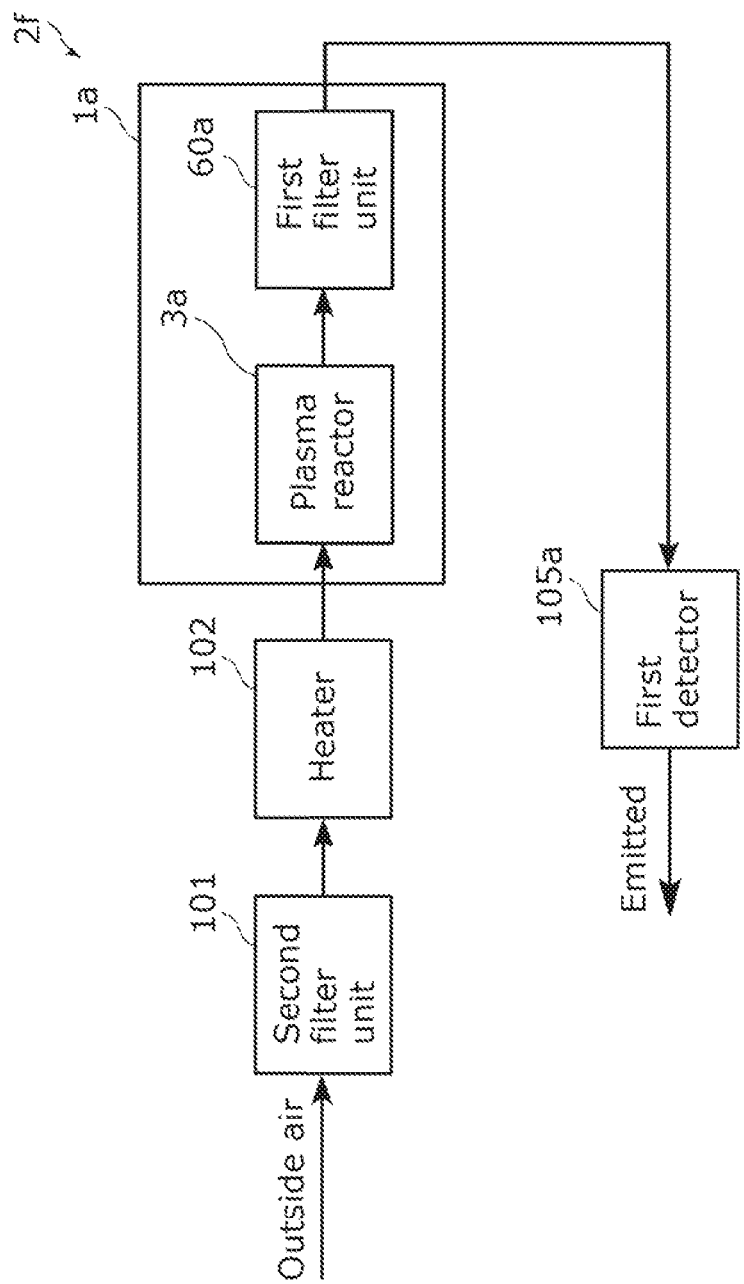
FIG. 11 is a block diagram illustrating an air purification system according to Variation 4 of Embodiment 2 which includes a second filter unit, a heater, and a first detector.

FIG. 11 is a block diagram illustrating air purification system 2f according to Variation 4 of Embodiment 2 which includes second filter unit 101, heater 102, and first detector 105a.

Air purification system 2f according to the present variation is different from the air purification system according to Variation 3 of Embodiment 2 in that main body 1a illustrated in FIG. 6 is used.

As illustrated in FIG. 11, main body 1a includes plasma reactor 3a and first filter unit 60a. Plasma reactor 3a includes first housing 10, linear electrode 20, power feeder 30, actuator 36, spectroscope 111, third dielectric 112, electric field probe 40, second amplifier 41, cymoscope 42, voltage converter 35, controller 70, and so on illustrated in FIG. 7.

<Variation 5>

Figure 12:
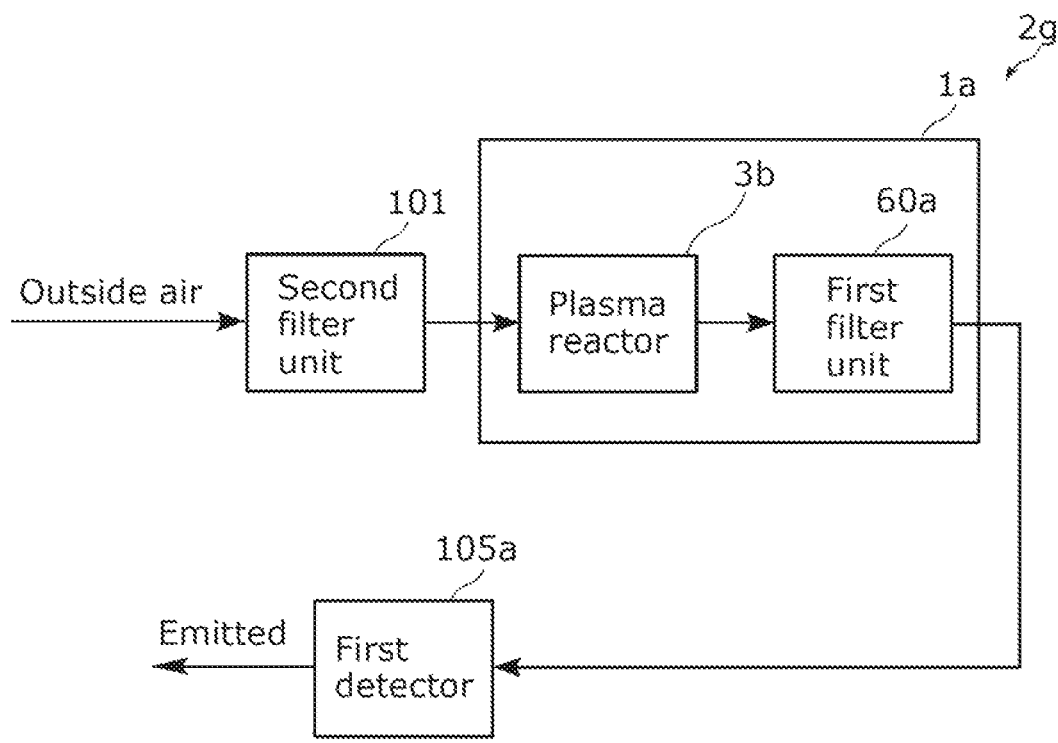
FIG. 12 is a block diagram illustrating an air purification system according to Variation 5 of Embodiment 2 which includes a second filter unit and a first detector.

FIG. 12 is a block diagram illustrating air purification system 2g according to Variation 5 of Embodiment 2 which includes second filter unit 101 and first detector 105a.

Air purification system 2g according to the present variation is different from the air purification system according to Variation 4 of Embodiment 2 in that the heater is not included.

As illustrated in FIG. 12, second filter unit 101 is connected to main body 1a, and the air that has passed through second filter unit 101 is taken into plasma reactor 3b of main body 1a.

<Variation 6>

Figure 13:
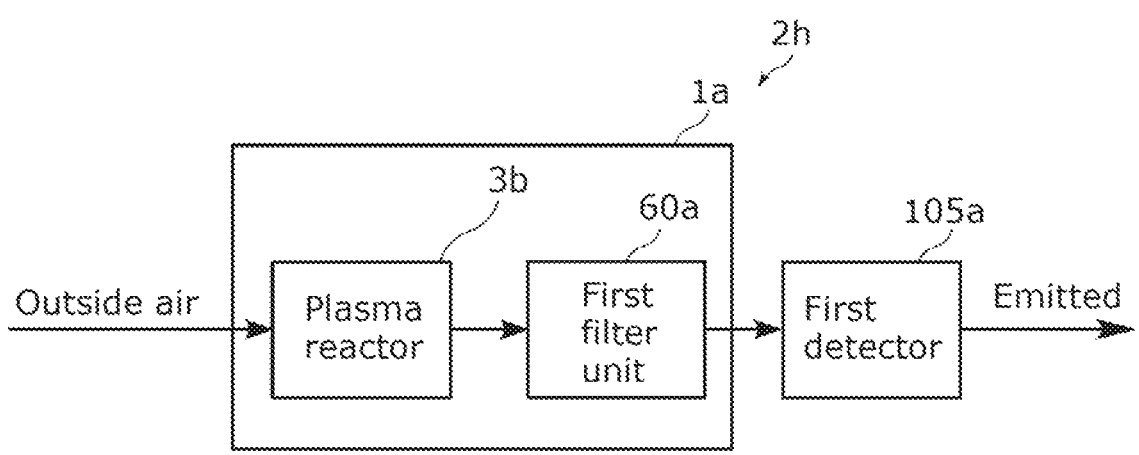
FIG. 13 is a block diagram illustrating an air purification system according to Variation 6 of Embodiment 2 which includes a first detector.

FIG. 13 is a block diagram illustrating air purification system 2h according to Variation 6 of Embodiment 2 which includes first detector 105a.

Air purification system 2h according to the present variation is different from the air purification system according to Variation 5 of Embodiment 2 in that the second filter unit is not included.

As illustrated in FIG. 13, plasma reactor 3b of main body 1a directly takes in the air, which is outside air in the surrounding environment.

Embodiment 3

Protective clothing 200 according to the present embodiment is described.

The present embodiment is different from Embodiment 1 in that it relates to protective clothing 200 that includes air purification system 100. A configuration of air purification system 100 according to the present embodiment is the same as the configuration of the air purification system according to Embodiment 1, and the same reference signs are given to the same constituent elements and detailed descriptions thereof are omitted.

Figure 14:
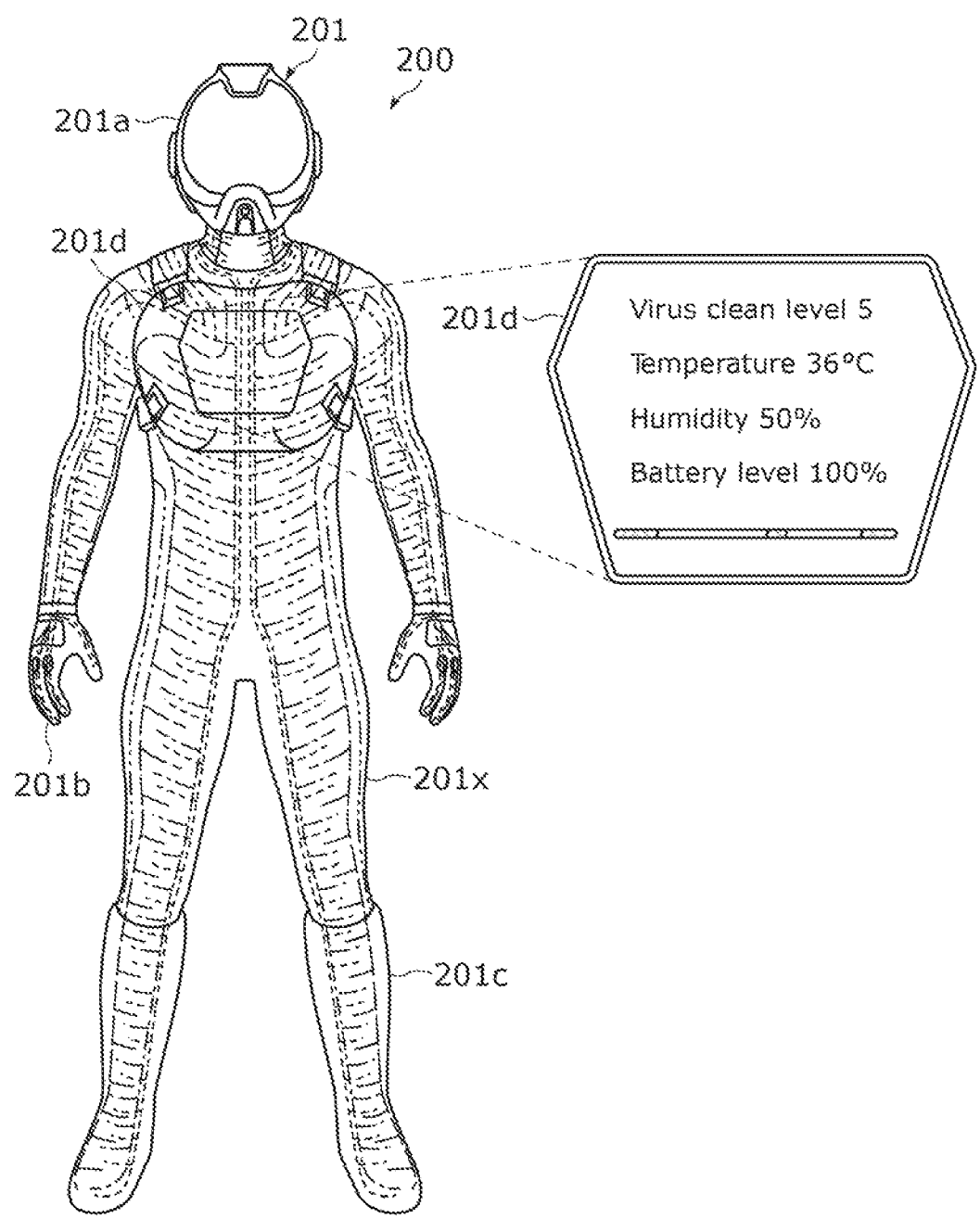
FIG. 14 is a schematic diagram illustrating a front view of protective clothing according to Embodiment 3 and a display of the protective clothing.
Figure 15:
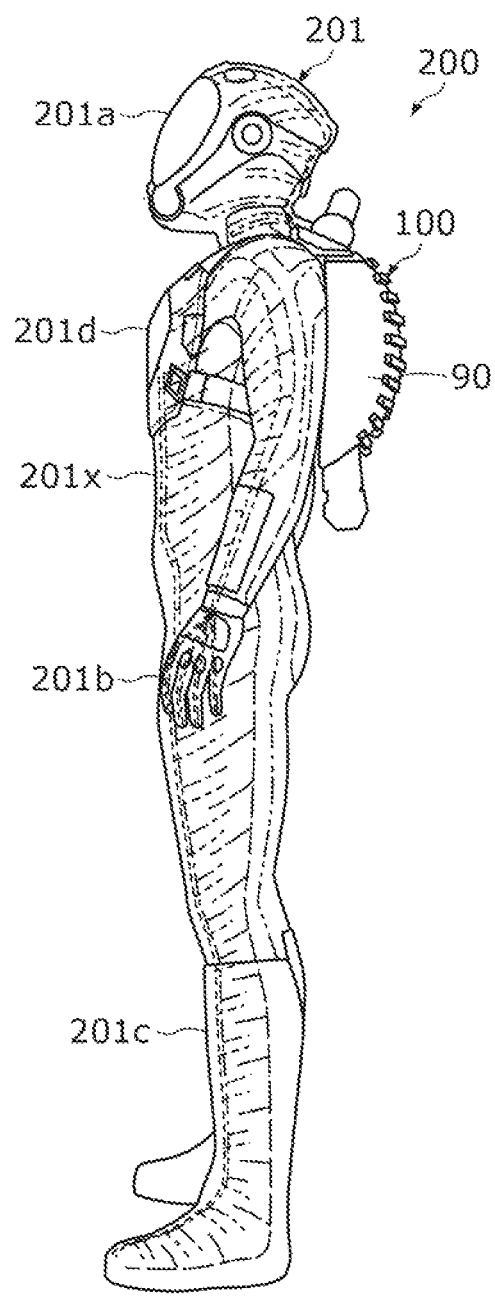
FIG. 15 is a side view of the protective clothing according to Embodiment 3 viewed from a lateral side.

FIG. 14 is a schematic diagram illustrating a front view of protective clothing 200 according to Embodiment 3 and display 201d of protective clothing 200. FIG. 15 is a side view of protective clothing 200 according to Embodiment 3 viewed from a lateral side.

As illustrated in FIG. 14 and FIG. 15, protective clothing 200 includes air purification system 100, covering body 201, and display 201d.

Air purification system 100 purifies the air taken in from the outside and supplies the purified air into covering body 201. That is to say, air purification system 100 purifies the air by decomposing and removing bacteria, viruses, etc. contained in the air, and supplies the purified air into covering body 201.

Covering body 201 is provided with air purification system 100 and covers the surface of the body of a person. Covering body 201 is capable of covering the entire body of a person and maintaining the inside sealed. Covering body 201 includes: outer cover 201x that covers the head, upper limb, body trunk, and lower limb of the person wearing covering body 201; helmet 201a to be worn over outer cover 201x to protect the head; gloves 201b that protect both hands; and boots 201c that protect both feet. Outer cover 201x and helmet 201a are joined by a joining component such as a joint. Outer cover 201x and gloves 201b are joined by another joining component. Outer cover 201x and boots 201c are joined by yet another joining component.

On the rear side of covering body 201, casing 90 that accommodates air purification system 100 is attached. Casing 90 is an exterior cover of air purification system 100. Casing 90 may be included in the configuration of protective clothing 200, and may be included in the configuration of air purification system 100.

Figure 16:
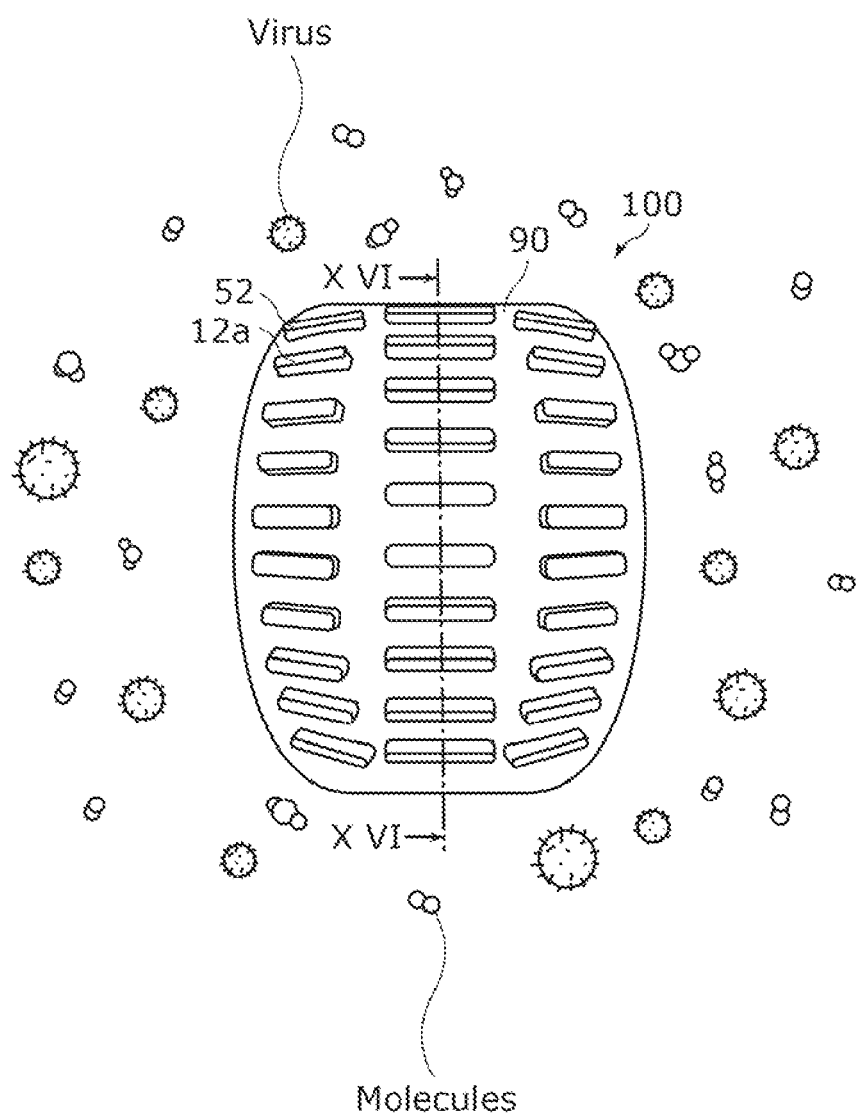
FIG. 16 is a front view of an air purification system included in the protective clothing according to Embodiment 3, illustrating how the air purification system takes in viruses etc. along with the air.
Figure 17:
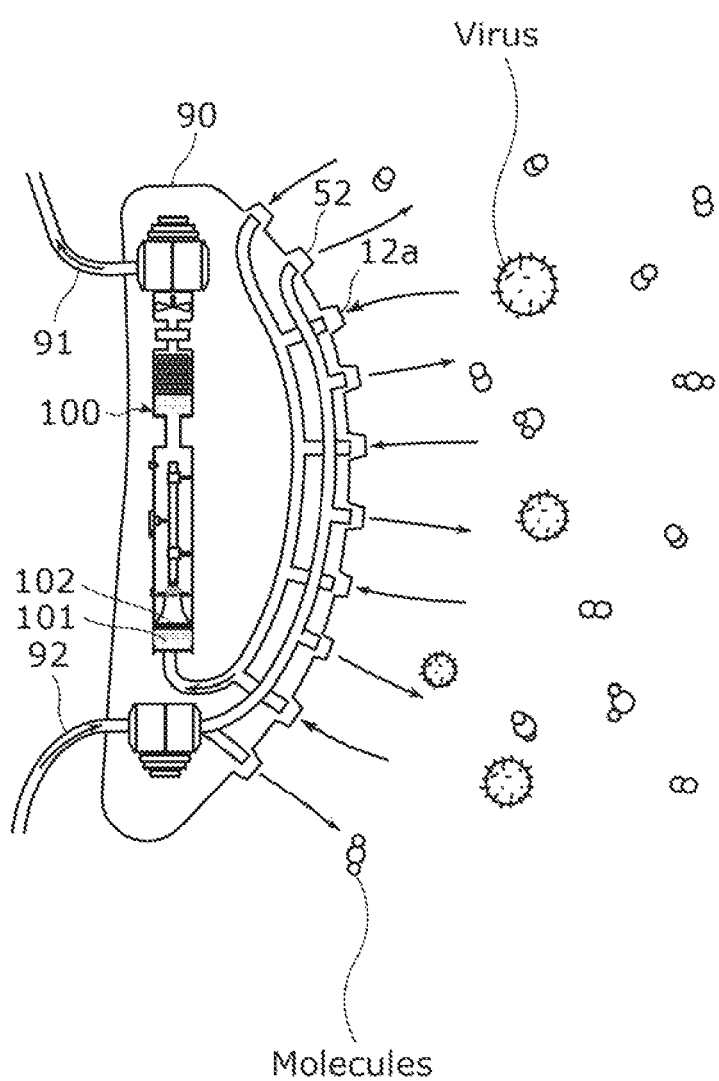
FIG. 17 is a cross-sectional view of the air purification system included in the protective clothing according to Embodiment 3 along line XVI-XVI in FIG. 16.

FIG. 16 is a front view of air purification system 100 included in protective clothing 200 according to Embodiment 3, illustrating how air purification system 100 takes in viruses etc. along with the air. FIG. 17 is a cross-sectional view of air purification system 100 included in protective clothing 200 according to Embodiment 3 along line XVI-XVI in FIG. 16. The arrows in FIG. 17 represent intake and discharge of the air.

As illustrated in FIG. 16 and FIG. 17, air purification system 100 takes in the ambient air through a plurality of inlets 12a formed on the rear side of casing 90 (the side opposite to the side where covering body 201 is provided). The air taken in is purified by air purification system 100 and supplied into protective clothing 200 through supply pipe 91. In addition, air purification system 100 discharges, through a plurality of outlets 52 formed on the rear side of casing 90, the air taken into covering body 201. The air in protective clothing 200 is discharged outside protective clothing 200 through supply pipe 92. With protective clothing 200, the air purified through air purification system 100 is supplied into protective clothing 200, and the air that a person breathed inside protective clothing 200 is discharged outside protective clothing 200. The supply of the purified air into protective clothing 200 and the discharge of the air are performed using a micro-pump unit, for example. In other words, the purified air is supplied and discharged so that the person can breathe inside protective clothing 200. Note that a carbon dioxide absorber capable of processing carbon dioxide discharged by a person through breathing may be provided inside casing 90.

In the present embodiment, the plurality of inlets 12a and the plurality of outlets 52 formed on the rear side of casing 90 are alternately arranged one by one. Note that the arrangement of inlets 12a and outlets 52 is not limited to the arrangement according to the present embodiment, and they may be alternately arranged two or more by two or more, for example.

Display 201d is a monitor attached to the front side of covering body 201. Display 201d displays information regarding the inside of covering body 201, for example. The information indicates, for example, the level of the purified air inside covering body 201, the temperature and humidity inside covering body 201, and the remaining battery level, etc. Display 201d displays the information by being controlled by controller 70 of air purification system 100.

Advantageous Effects

Advantageous effects of protective clothing 200 according to the present embodiment are described.

As described above, protective clothing 200 according to the present embodiment includes air purification system 100 and covering body 201 that is provided with air purification system 100 and that covers the surface of the body of a person. Air purification system 100 purifies the air taken in from the outside and supplies the purified air into covering body 201.

This allows the person to act safely even in an environment where bacteria, viruses, etc. are suspended in the air.

In addition, protective clothing 200 also yields the same advantageous effects as those of Embodiment 1 etc. described above.

Other Variations Etc

Although the present disclosure has been described above based on Embodiments 1 to 3, the present disclosure is not limited to Embodiments 1 to 3.

For example, the air purification system and the protective clothing including the air purification system according to Embodiments 1 to 3 are designed to increase the Q factors of the resonators of the linear electrode and the first housing. The Q factor of the resonance is determined by the ratio between the resistance of the linear electrode and the resistance of the power feeding line (input power loss).

For example, the air purification system according to Embodiment 2 may include the plasma reactor and the first filter unit as illustrated in FIG. 7.

The present disclosure also encompasses other forms achieved by making various modifications conceivable to those skilled in the art to Embodiments 1 to 3, as well as forms implemented by freely combining constituent elements and functions of Embodiments 1 to 3 without departing from the essence of the present disclosure.

INDUSTRIAL APPLICABILITY

The air purification system and the protective clothing including the air purification system according to the present disclosure can be used in apparatuses such as air purifiers, and can be used for activities in areas where bacteria, viruses, etc. are prevalent.

The invention claimed is:

1. An air purification system that generates plasma using voltage, the air purification system comprising:
 a first electrode that generates electromagnetic resonance when power is supplied;
 a second electrode disposed surrounding the first electrode in a state of being separated from the first electrode;
 a power feeder that supplies power to the first electrode;

an electric field probe that measures an intensity of an electric field between the first electrode and the second electrode; and a controller that controls the power supplied to the first electrode, wherein the controller performs control by adjusting a frequency of the power supplied to the first electrode and a position at which the power is supplied to the first electrode, to cause a half wavelength during electromagnetic resonance of the first electrode to be a sum of a length of the first electrode and a length of plasma generated, and maximize an output value of a signal indicating the intensity of the electric field measured by the electric field probe.

2. The air purification system according to claim 1,
wherein the controller obtains, from a detector, a measurement result of a content of ozone contained in air that has passed through a region between the first electrode and the second electrode, and based on the measurement result obtained, performs control by adjusting the power supplied, to (i) cause an amount of ozone generated due to plasma generation to become constant at all times and (ii) apply an energy having an intermediate value between a dissociation energy of oxygen molecules and a dissociation energy of nitrogen molecules, at which nitrogen oxides are substantially not generated.

3. The air purification system according to claim 2,
wherein the power supplied to the first electrode is alternating current (AC) power, and
the controller performs control by adjusting an amplitude of the AC power supplied, to cause the amount of ozone generated to become constant at all times.

4. The air purification system according to claim 3,
wherein a waveform of the AC power supplied to the first electrode is a waveform obtained by performing amplitude modulation on a carrier wave, and
the controller performs control by adjusting the amplitude modulation, to cause the amount of ozone generated to become constant.

5. The air purification system according to claim 4,
wherein the waveform of the AC power supplied to the first electrode is a waveform obtained by performing amplitude modulation on a carrier wave, and
the controller performs control to cause the amount of ozone generated to become constant, by adjusting the amplitude modulation to cause a value of the amplitude modulation to intermittently repeat a given value and zero.

6. The air purification system according to claim 1,
wherein the controller performs control by adjusting the power supplied, to cause a concentration of ozone generated to be less than or equal to 0.1 ppm.

7. The air purification system according to claim 1, comprising:
an actuator that changes a position of a power feeding point at which the power feeder supplies the power to the first electrode,
wherein the controller adjusts the position of the power feeding point by operating the actuator.

8. The air purification system according to claim 7,
wherein the controller performs control by adjusting two parameters, namely the frequency and the position of the power feeding point on the first electrode, to cause an output voltage of the electric field probe to reach a local maximum.

9. The air purification system according to claim 1,
wherein the second electrode is a housing including an inlet through which air is taken in,
the air purification system comprising:
a filter that is disposed in vicinity of an outlet through which the air taken in through the inlet is discharged, and that, when the air taken in through the inlet passes through, removes a nitrogen oxide and ozone generated by a plasma reactor including the first electrode and the second electrode.

10. The air purification system according to claim 9,
wherein the controller adjusts input power inputted to a plasma reactor, to apply a dissociation energy of oxygen molecules contained in the air taken in through the inlet.

11. The air purification system according to claim 1,
wherein the first electrode is an elongated electrode,
the second electrode forms, in a longitudinal direction of the first electrode, a space that is elongated and accommodates the first electrode, and
in the space, a plasma generation region for generating plasma is provided between the first electrode and an inlet of the second electrode.

12. The air purification system according to claim 1,
wherein plasma is generated using power having a waveform obtained by performing amplitude modulation on a carrier wave having a frequency in a range of from 100 MHz to 10 GHz, to cause an amount of ozone generated to become constant.

13. Protective clothing comprising:
the air purification system according to claim 1; and
a covering body that is provided with the air purification system and covers a surface of a body of a person,
wherein the air purification system purifies air taken in from outside and supplies purified air into the covering body.

* * * * *